(12) United States Patent
Chan et al.

(10) Patent No.: US 11,339,175 B2
(45) Date of Patent: May 24, 2022

(54) THIOL-BASED FLUORESCENT PROBE FOR REACTIVE SPECIES

(71) Applicant: The Board of Trustees of the University of Illinois, Urbana, IL (US)

(72) Inventors: Jefferson Chan, Savoy, IL (US); Nicholas William Pino, Tyaskin, MD (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 89 days.

(21) Appl. No.: 16/675,859

(22) Filed: Nov. 6, 2019

(65) Prior Publication Data

US 2020/0140452 A1    May 7, 2020

Related U.S. Application Data

(60) Provisional application No. 62/756,389, filed on Nov. 6, 2018.

(51) Int. Cl.
*G01N 21/77*    (2006.01)
*G01N 33/52*    (2006.01)
(Continued)

(52) U.S. Cl.
CPC .......... *C07D 493/10* (2013.01); *C07D 311/16* (2013.01); *G01N 21/77* (2013.01);
(Continued)

(58) Field of Classification Search
CPC .......... Y10T 436/177692; G01N 21/77; G01N 33/52; G01N 2021/7786; C07D 493/10; C07D 311/16
See application file for complete search history.

(56) References Cited

U.S. PATENT DOCUMENTS 9,494,592 B2 * 11/2016 Xian .................... C07D 311/16

FOREIGN PATENT DOCUMENTS

| CN | 105017298 A | 11/2015 |
| KR | 20190085401 A | 7/2019 |
| WO | 2018104963 A1 | 6/2018 |

OTHER PUBLICATIONS

Pino, N.W. et al. "NitroxylFluor: A Thiol-Based Fluorescent Probe for Live-Cell Imaging of Nitroxyl," J. Am. Chem. Soc. 2017, 139, 18476-18479 and Supporting Information. Published: Dec. 14, 2017. (Year: 2017).*

(Continued)

*Primary Examiner* — Jennifer Wecker
*Assistant Examiner* — Michelle Adams
(74) *Attorney, Agent, or Firm* — Haukaas Fortius PLLC; Michael H. Haukaas

(57) ABSTRACT

Detection of nitroxyl (HNO), the transient one-electron reduced form of nitric oxide, is a significant challenge owing to its high reactivity with biological thiols (rate constants as high as $10^9 M^{-1} s^{-1}$). Reported herein is a new thiol-based HNO-responsive trigger that can compete against reactive thiols for HNO. This process forms an N-hydroxysulfenamide intermediate which cyclizes to release a masked fluorophore leading to fluorescence enhancement. To ensure a rapid cyclization step, the disclosed design capitalizes on two established physical organic phenomena: the alpha-effect and the Thorpe-Ingold effect. Using this new trigger, NitroxylFluor was developed; a selective HNO-responsive fluorescent probe. Treatment of NitroxylFluor with an HNO donor results in a 16-fold turn-on. This probe also exhibits excellent selectivity over various reactive nitrogen, oxygen, and sulfur species and efficacy in the presence of thiols (e.g., glutathione in mM concentrations). Also, live cell imaging of HNO using NitroxylFluor was performed.

18 Claims, 7 Drawing Sheets

(51) Int. Cl.
*C07D 493/10* (2006.01)
*C07D 311/16* (2006.01)
(52) U.S. Cl.
CPC ..... *G01N 33/52* (2013.01); *G01N 2021/7786* (2013.01); *Y10T 436/177692* (2015.01)

(56) References Cited

OTHER PUBLICATIONS

"Nick, Jerome and Martin's paper is accepted for publication in JACS!" webpage at <https://www.chan-lab.com/single-post/2017/12/06/Nick-Jerome-and-Martins-paper-is-accepted-for-publication-in-JACS> (Dec. 6, 2017), downloaded on Jun. 16, 2021. (Year: 2017).*

@ChanLabUIUC (Dec. 6, 2017) Just accepted! NitroxylFluor, our thiol-based probe for nitroxyl imaging, will appear in JACS. Congrats all! [Tweet] <https://twitter.com/ChanLabUIUC/status/938489053913239552> downloaded on Jun. 16, 2021 (Year: 2017).*

Smulik-Izydorczyk, R. et al. "Fluorescent probes for the detection of nitroxyl (HNO)," Free Radical Biology and Medicine 128 (2018) 69-83. Available online Apr. 25, 2018 (Year: 2018).*

Yan, J. et al. "Self-immolative colorimetric, fluorescent and chemiluminescent chemosensors," Chem. Soc. Rev., 2018, 47, 6900. Published on Sep. 3, 2018. (Year: 2018).*

Apfel et al., "Detection of Nitric Oxide and Nitroxyl with Benzoresorufin-Based Fluorescent Sensors," Inorg. Chem., 52(6):3285-3294, Mar. 2013.

Chan et al., "Reaction-Based Small-Molecule Fluorescent Probes for Chemoselective Bioimaging," Nat Chem., 4:973-984, Nov. 2012.

Miao et al., "Recent Advances in the Chemical Biology of Nitroxyl (HNO) Detection and Generation," Nitric Oxide, 57:1-14, Jul. 2016.

Reisz et al., "Reductive Phosphine-Mediated Ligation of Nitroxyl (HNO)," Org. Lett., 11(13):2719-2721, Jun. 2009.

Rivera-Fuentes et al., "Metal-Based Optical Probes for Live Cell Imaging of Nitroxyl (HNO)," Acc. Chem. Res., 48(11):2927-2934, Nov. 2015.

Rosenthal et al., "Direct Detection of Nitroxyl in Aqueous Solution Using a Tripodal Copper(II) BODIPY Complex," J. Am. Chem. Soc., 132(16):5536-5537, Mar. 2010.

Wrobel et al., "A Fast and Selective Near-Infrared Fluorescent Sensor for Multicolor Imaging of Biological Nitroxyl (HNO)," J. Am. Chem. Soc., 136(12):4697-4705, Feb. 2014.

Zhou et al., "Visualization of Nitroxyl in Living Cells by a Chelated Copper(II) Coumarin Complex," Org. Lett., 13(6):1290-1293, Feb. 2011.

* cited by examiner

THIOL-BASED FLUORESCENT PROBE FOR REACTIVE SPECIES

RELATED APPLICATIONS

This application claims priority under 35 U.S.C. § 119(e) to U.S. Provisional Patent Application No. 62/756,389, filed Nov. 6, 2018, which is incorporated herein by reference.

BACKGROUND OF THE INVENTION

Nitroxyl (HNO), the one-electron reduced derivative of nitric oxide (NO), has emerged as a potential therapeutic agent for the treatment of cardiovascular disorders due to its unique ability to increase cardiac output by decreasing venous resistance. HNO is also recognized to protect against myocardial ischemia-reperfusion injury and has gained attention as a possible anti-cancer agent. The cellular production of HNO is proposed to involve either non-enzymatic or enzymatic mechanisms. For example, HNO has been generated via reduction of NO by thiols, or enzymatic reduction of 1-arginine by nitric oxide synthase (NOS) under tetrahydrobiopterin-free conditions. It is also speculated that hydroxylamine and N-hydroxy-1-arginine may be oxidized to produce HNO in reactions mediated by heme proteins, such as peroxidases.

The detection of HNO in a biological context is an immense challenge due to its highly reactive chemical nature. For instance, HNO can spontaneously dimerize and dehydrate in a sequence that affords $N_2O$ ($k=8\times10^6 M^{-1} s^{-1}$). HNO can also act as a potent electrophile in a reaction with nucleophilic biological thiols to form N-hydroxysulfenamide intermediates (FIG. 1a). The rate constants for this reaction range from $2\times10^6 M^{-1} s^{-1}$, for low molecular weight thiols (e.g., glutathione (GSH)) to greater than $10^9 M^{-1} s^{-1}$ for proteins exhibiting a low thiol pKa (e.g., glyceraldehyde 3-phosphate dehydrogenase). Once formed the N-hydroxysulfenamide intermediate can rearrange to a sulfinamide product or react with another thiol to yield a disulfide (FIG. 1a). Thus, any detection strategy must proceed with comparable kinetics to intercept HNO before it is metabolized.

A promising approach to detect analytes in general is to utilize reaction-based probes which couple fluorescent enhancement with analyte-associated reactivity. In the context of HNO sensing, a variety of reaction-based HNO probes for fluorescence imaging have been developed. Such probes are based on either redox coordination or phosphine-mediated Staudinger chemistry (*Org Lett* 2009, 11, 2719). However, metal-based HNO fluorescent probes are limited by slow reaction kinetics relative to thiols and exhibit small dynamic range (typically less than 5-fold fluorescent turn-on). Phosphine-based probes suffer from reduced sensitivity because for every equivalent of HNO, two probes are required for sensing since one equivalent is consumed to generate an unproductive phosphine oxide by-product. Additionally, some phosphine-based probes also exhibit cross-reactivity with NO donors.

Accordingly, there is a need for a sensitive method to selectively detect reactive species such as nitroxyl while minimizing interference from competing biologically relevant nitroxyl traps such as glutathione.

SUMMARY

Herein is reported the rational design of a new bioinspired thiol-based trigger for the development of a series of HNO-responsive fluorescent probes (FIG. 1b). The probes demonstrate excellent selectivity against a panel of reactive oxygen species, reactive sulfur species and reactive nitrogen species, as well as efficacy for HNO detection in competition experiments in the presence of biological thiols. This disclosure demonstrates probes, such as NitroxylFluor, for successfully imaging HNO in living cells, for example, MDA-MB-231 human breast adenocarcinoma cells.

Accordingly, this disclosure provides a compound of Formula I:

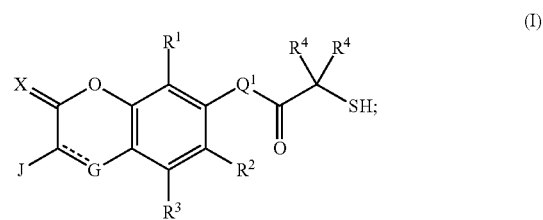

or a salt or solvate thereof, wherein
- ------- is a single bond or a double bond;
- $Q^1$ is O or S;
- $R^1$, $R^2$, and $R^3$ are each independently H, halo, —($C_1$-$C_6$)alkyl, or OR wherein R is H or —($C_1$-$C_6$)alkyl;
- each $R^4$ is independently H or —($C_1$-$C_6$)alkyl, or each $R^4$ taken together form —($C_3$-$C_6$)cycloalkyl;
- G is —CH— or —C[($C_1$-$C_6$)alkyl]— when ------- is a double bond, or G is Formula IA when ------- is a single bond:

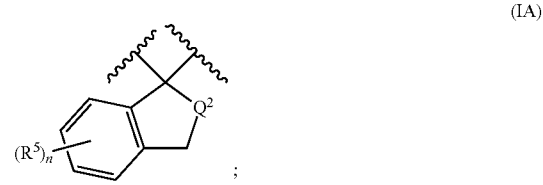

wherein
- $Q^2$ is O or S;
- each $R^5$ is independently H, halo, —($C_1$-$C_6$)alkyl, or $OR^a$ wherein $R^a$ is H or —($C_1$-$C_6$)alkyl; and n is 1-4;
- X is O, and J is H or —($C_1$-$C_6$)alkyl when ------- is a double bond; and
- X and J taken together form a monocyclic aryl group when ------- is a single bond;
- wherein the bonds in Formula I that form the monocyclic aryl group are aromatic and the monocyclic aryl group is optionally substituted with one or more substituents.

This disclosure also provides a method for imaging nitroxyl comprising:
a) contacting a sample with a compound of Formula I or a compound otherwise described herein, to form a mixture; and
b) detecting the presence or absence of a change in fluorescent intensity in the mixture;
wherein the thiol moiety of the compound covalently bonds to nitroxyl when present in the sample to form a —S(NH)OH intermediate, and the intermediate intramolecularly cyclizes at the carbonyl moiety (—C(=O)—) and cleaves the $Q^1$-carbonyl bond to release a xanthene moiety or a coumarin moiety as a fluorescent molecule;

thereby imaging nitroxyl in the sample when the fluorescent molecule changes the fluorescent intensity of the mixture.

In some aspects of the above method, the fluorescent molecule is Formula Y or Formula Z:

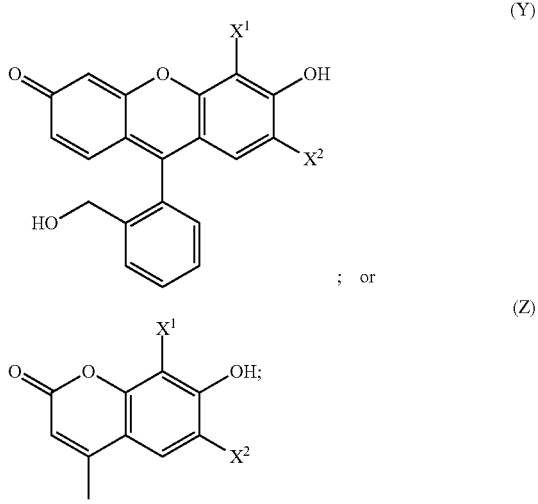

wherein $X^1$ and $X^2$ are independently H or halo.

Additionally, this disclosure provides a method for detecting a reactive chemical species comprising:

a) contacting a sample with a compound of Formula IV to form a mixture:

MF-CL-AG-NU           (IV);

wherein
  MF is a moiety capable of fluorescence;
  CL is an electrophilic cleavable linking moiety;
  AG is a Thorpe-Ingold accelerating group; and
  NU is a nucleophile; and b) detecting the presence or absence of a change in fluorescent intensity in the mixture;

wherein NU covalently bonds to a reactive chemical species when present in the sample to form a nucleophilic intermediate comprising an alpha-effect, and the nucleophilic intermediate intramolecularly cyclizes at CL and cleaves the MF—CL bond to release MF as a fluorescent molecule;

thereby detecting the reactive chemical species in the sample when the fluorescent molecule changes the fluorescent intensity of the mixture.

The invention provides novel compounds of Formulas I-IV, intermediates for the synthesis of compounds of Formulas I-IV, as well as methods of preparing compounds of Formulas I-IV. The invention also provides compounds of Formulas I-IV that are useful as intermediates for the synthesis of other useful compounds. The invention provides for the use of compounds of Formulas I-IV for the manufacture of diagnostics and for use in a subject such as a human.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
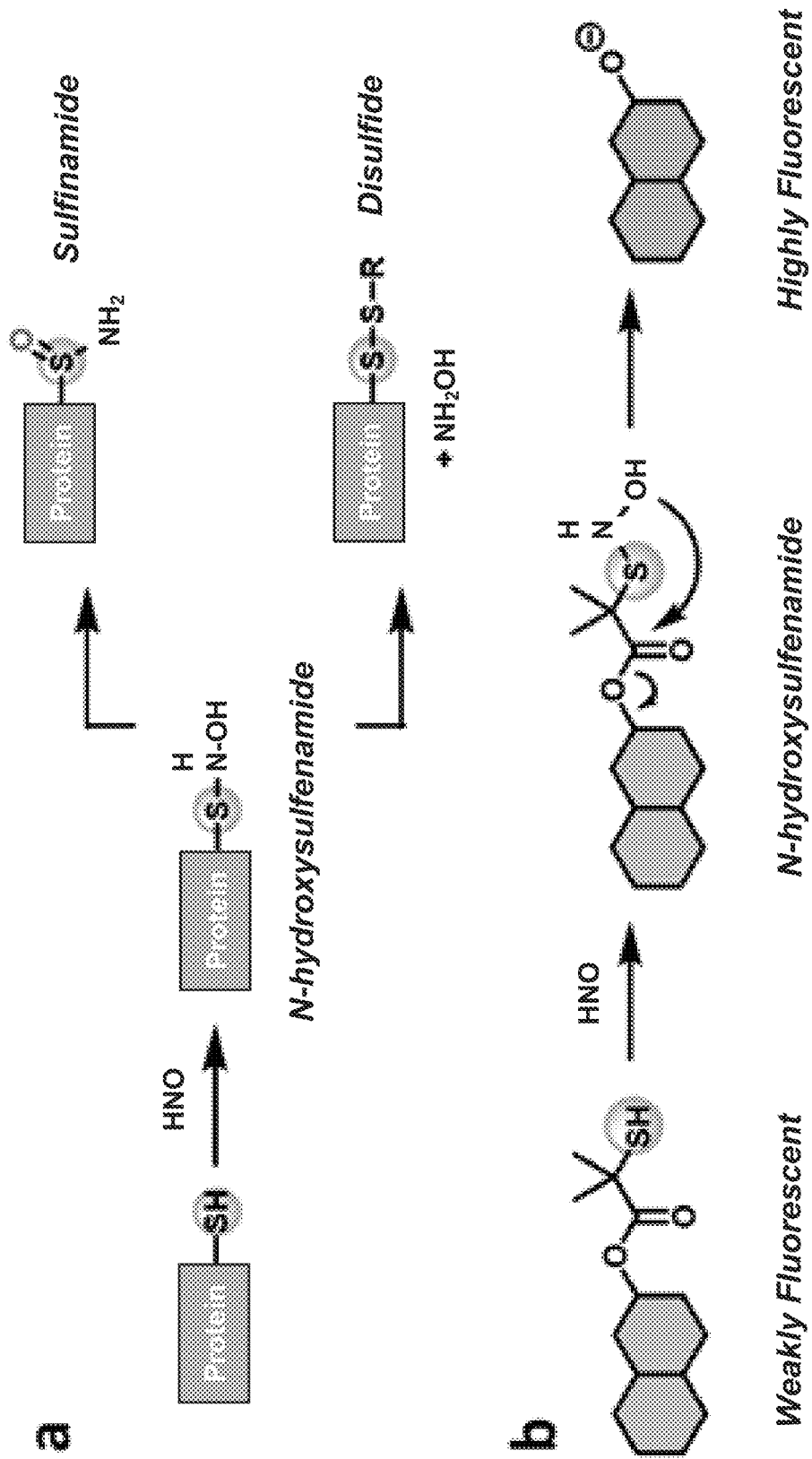
FIG. 1. a) HNO reacts with protein thiols to form an N-hydroxysulfenamide intermediate, which rearranges to a sulfinamide or is attacked by another thiol to form a disulfide. b) HNO reacts with the disclosed thiol-based trigger in the same fashion to afford a common N-hydroxysulfenamide intermediate which cyclizes to release the masked dye.

It was proposed that for any HNO-responsive trigger to be competent in a biological setting, it must exhibit sufficient reactivity with HNO to compete against abundant biological thiols present in the cellular milieu. An initial design featured a 2-mercaptoacetate trigger that can be used to cap the hydroxyl group on various dye platforms to quench its fluorescence (Scheme 1a). In the absence of HNO, it was anticipated that the cyclization to release the dye would be unlikely since the product would be a strained alpha-thiolactone. However, reaction with HNO was hypothesized to yield a highly reactive nucleophile (N-hydroxysulfenamide intermediate) that could readily cyclize due to the lone-pair electrons on the nitrogen atom, which enhances the nucleophilicity of the adjacent —OH group (alpha-effect).

Scheme 1. Chemical structures of a) the NitroBlue series and b) NitroxylFluor and the fluorescent turned over product.

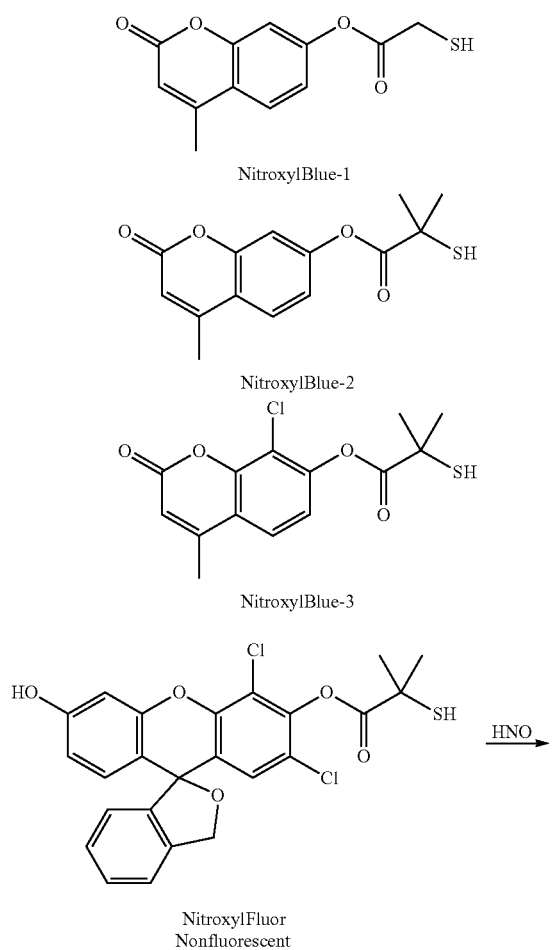

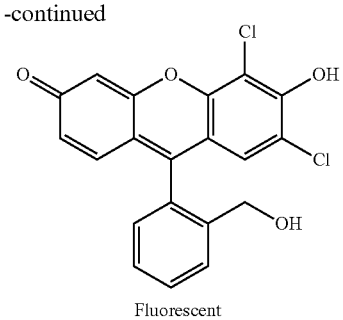

Fluorescent

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with therapeutic drugs.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983).

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

Embodiments of the Invention

This disclosure provides embodiments of a compound of Formula I:

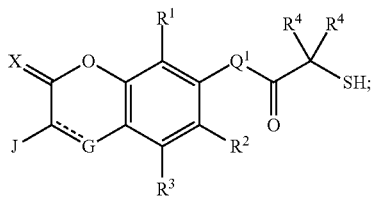
(I)

or a salt or solvate thereof, wherein
- - - - - is a single bond or a double bond;
$Q^1$ is O or S;
$R^1$, $R^2$, and $R^3$ are each independently H, halo, —($C_1$-$C_6$)alkyl, or OR wherein R is H or —($C_1$-$C_6$)alkyl;
each $R^4$ is independently H or —($C_1$-$C_6$)alkyl, or each $R^4$ taken together form —($C_3$-$C_6$)cycloalkyl;
G is —CH— or —C[($C_1$-$C_6$)alkyl]— when - - - - - is a double bond, or G is Formula IA when - - - - - is a single bond:

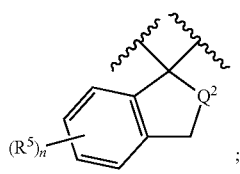
(IA)

wherein
$Q^2$ is O or S;
each $R^5$ is independently H, halo, —($C_1$-$C_6$)alkyl, or $OR^a$ wherein $R^a$ is H or —($C_1$-$C_6$)alkyl; and
n is 1-4;
X is O, and J is H or —($C_1$-$C_6$)alkyl when - - - - - is a double bond; and
X and J taken together form a monocyclic aryl group when - - - - - is a single bond;
wherein the bonds in Formula I that form the monocyclic aryl group are aromatic and the monocyclic aryl group is optionally substituted with one or more substituents.

In various embodiments, the compound of Formula I is a compound of Formula II:

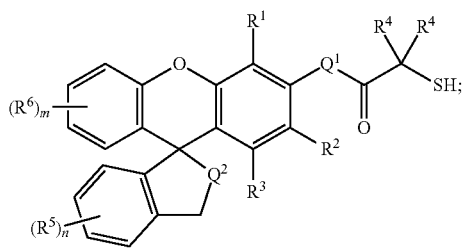
(II)

wherein
each $R^6$ is independently H, halo, —($C_1$-$C_6$)alkyl, or $OR^b$ wherein $R^b$ is H or —(C1-C6)alkyl; and
m is 1-4.

In other embodiments, the compound of Formula II is a compound of Formula IIB:

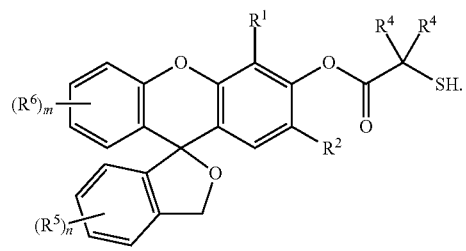
(IIB)

In additional embodiments, the compound of Formula II is a compound of Formula IIC:

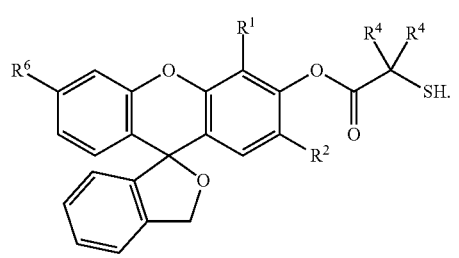
(IIC)

In yet other embodiments, $R^1$ and $R^2$ are each independently H, halo, OH, or —O($C_1$-$C_6$)alkyl; $R^4$ is —($C_1$-$C_6$)alkyl, or each $R^4$ taken together form —($C_3$-$C_6$)cycloalkyl; and $R^6$ is halo OH, or —O($C_1$-$C_6$)alkyl. In further embodiments, $R^1$ and $R^2$ are halo; $R^4$ is —($C_1$-$C_6$)alkyl, or each $R^4$ taken together form —($C_3$-$C_6$)cycloalkyl; and $R^6$ is halo or OH. In some other embodiments, $R^1$ and $R^2$ are chloro; $R^4$ is —$CH_3$; and $R^6$ is OH. For example, the compound is:

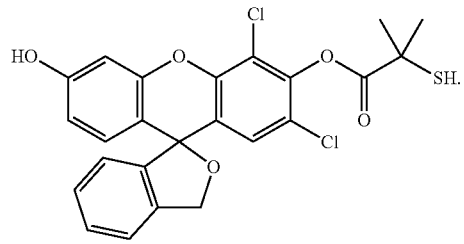 [SMILES: CC(C)(S)C(=O)Oc1c(Cl)cc2c(c1Cl)Oc1cc(O)ccc1C21OCc2ccccc21]

In various other embodiments, the compound of Formula I is a compound of Formula III:

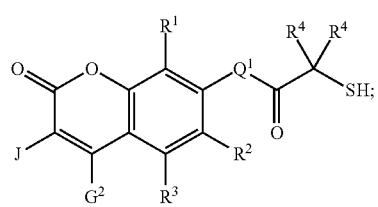
(III)

wherein
$R^1$, $R^2$, and $R^3$ are each independently H, halo, or —($C_1$-$C_6$)alkyl;
each $R^4$ is independently H or —($C_1$-$C_6$)alkyl, or each $R^4$ taken together form —($C_3$-$C_6$)cycloalkyl;

$G^2$ is H or —($C_1$-$C_6$)alkyl; and

J is H or —($C_1$-$C_6$)alkyl.

In yet some other embodiments, $Q^1$ is O. In further embodiments, $R^1$ and $R^2$ are each independently H or halo. In other embodiments, $R^3$ is H and $G^2$ is —($C_1$-$C_6$)alkyl. In further embodiments, J is H. In additional embodiments, $Q^1$ is O; $R^1$ and $R^2$ are each independently H or halo; $R^3$ and J are H; and $R^4$ and $G^2$ are —$CH_3$.

This disclosure also provides a method for imaging nitroxyl comprising:
  a) contacting a sample with a compound according to any one of Formulas I-III to form a mixture; and
  b) detecting the presence or absence of a change in fluorescent intensity in the mixture;
  wherein the thiol moiety of the compound covalently bonds to nitroxyl when present in the sample to form a —S(NH)OH intermediate, and the intermediate intramolecularly cyclizes at the carbonyl moiety (—C(=O)—) and cleaves the $Q^1$-carbonyl bond to release a xanthene moiety or a coumarin moiety as a fluorescent molecule;
  thereby imaging nitroxyl in the sample when the fluorescent molecule changes the fluorescent intensity of the mixture.

In some additional embodiments, the fluorescent molecule is Formula Y or Formula Z:

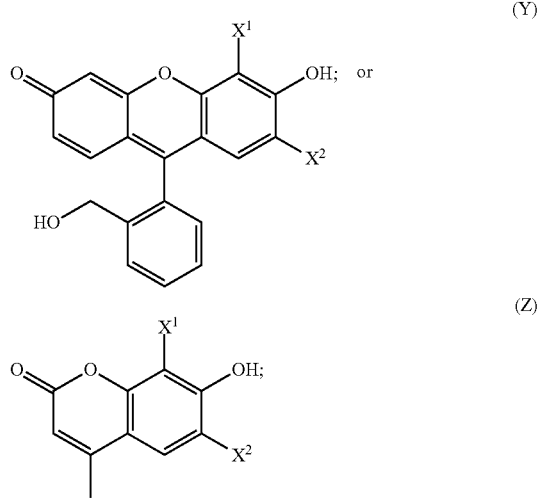

wherein $X^1$ and $X^2$ are independently H or halo.

In various embodiments, the fluorescence of the fluorescent molecule is greater than the fluorescence of the probe. In additional embodiments, the fluorescent molecule has an absorbance and emission profile that is in the visible spectrum. In further embodiments, the probe is more reactive toward nitroxyl than biological thiols.

Additionally, this disclosure provides a method for detecting a reactive chemical species comprising:
  a) contacting a sample with a compound of Formula IV to form a mixture:

MF-CL-AG-NU  (IV);

wherein
    MF is a moiety capable of fluorescence;
    CL is an electrophilic cleavable linking moiety;
    AG is a Thorpe-Ingold accelerating group; and
    NU is a nucleophile; and
  b) detecting the presence or absence of a change in fluorescent intensity in the mixture;
  wherein NU covalently bonds to a reactive chemical species when present in the sample to form a nucleophilic intermediate comprising an alpha-effect, and the nucleophilic intermediate intramolecularly cyclizes at CL and cleaves the MF—CL bond to release MF as a fluorescent molecule;
  thereby detecting the reactive chemical species in the sample when the fluorescent molecule changes the fluorescent intensity of the mixture.

In various embodiments, NU is thiol (—SH) and the reactive chemical species is nitroxyl (HNO). In other embodiments, the Thorpe-Ingold accelerating group (AG) comprises a gem-($C_1$-$C_8$)dialkyl moiety or a ($C_3$-$C_8$)cycloalkyl moiety.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2, 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion

Figure 4:
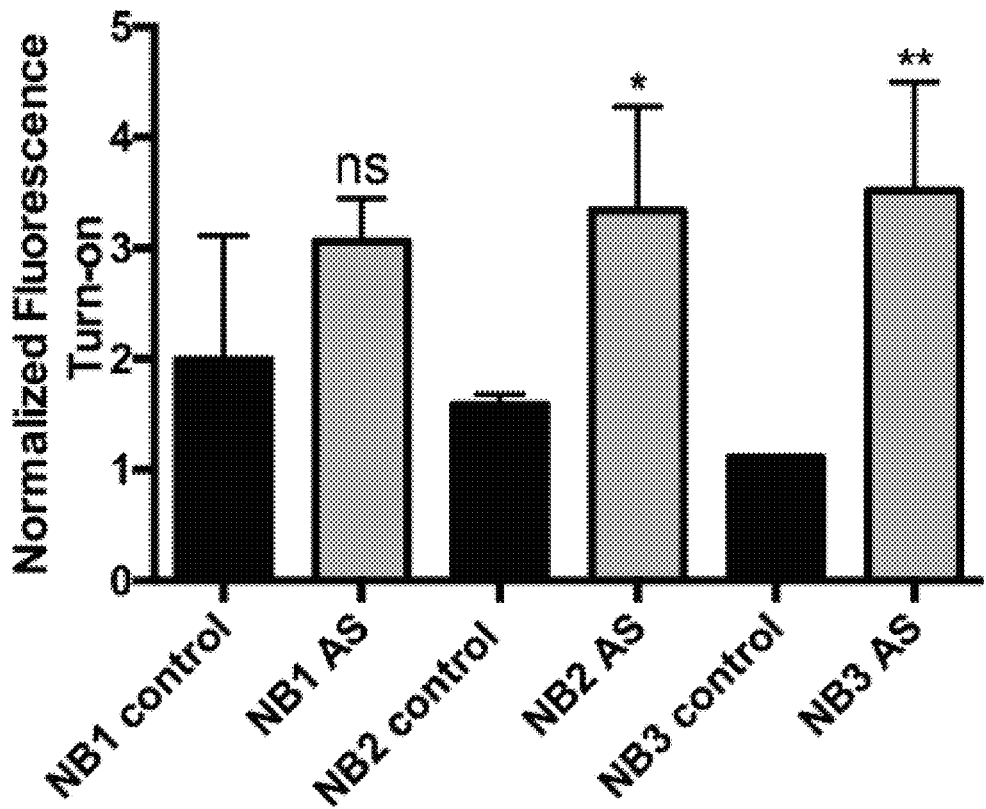
FIG. 4. The normalized fluorescence turn-on response of NitroxylBlue-1, -2, and -3 treated with a vehicle control and incubated in PBS at 37° C. are shown in black. The normalized fluorescence turn-on response of NitroxylBlue-1, -2, and -3 treated with 100 μM Angeli's salt are shown in green. All data was taken 10 minutes after treatment. Statistical significance measured with respect to the corresponding control. *, $p<0.05$; **, $p<0.01$. (n=3).

With the above design in mind NitroxylBlue-1 (NB-1) was developed, a coumarin-based HNO probe featuring a 2-mercaptoacetate trigger (Scheme 1a). The maximum absorbance and emission of NB-1 were centered at 350 nm and 448 nm, respectively. The probe itself was weakly fluorescent indicating efficient fluorescent quenching. Ten minutes after treatment with Angeli's salt, an HNO donor, insignificant fluorescence enhancement over the background was observed (FIG. 4). It was speculated that the lack of response was due to cyclization kinetics that were too slow. Additionally, it was observed that the ester moiety was prone to hydrolysis (~2-fold turn-on after 10 minutes at 37° C.), which can lead to false positives (FIG. 4). To address these shortcomings an α-geminal dimethyl group to afford NitroxylBlue-2 (NB-2) was installed (Scheme 1a). This modification was made to increase stability by shielding the ester from hydrolysis with greater steric bulk. Also, the Thorpe-Ingold effect was leveraged, which describes the acceleration of cyclization from the substitution of hydrogen atoms for alkyl groups on the carbons tethering two reaction centers (*Chemical Reviews* 2005, 105, 1735).

Figure 5:
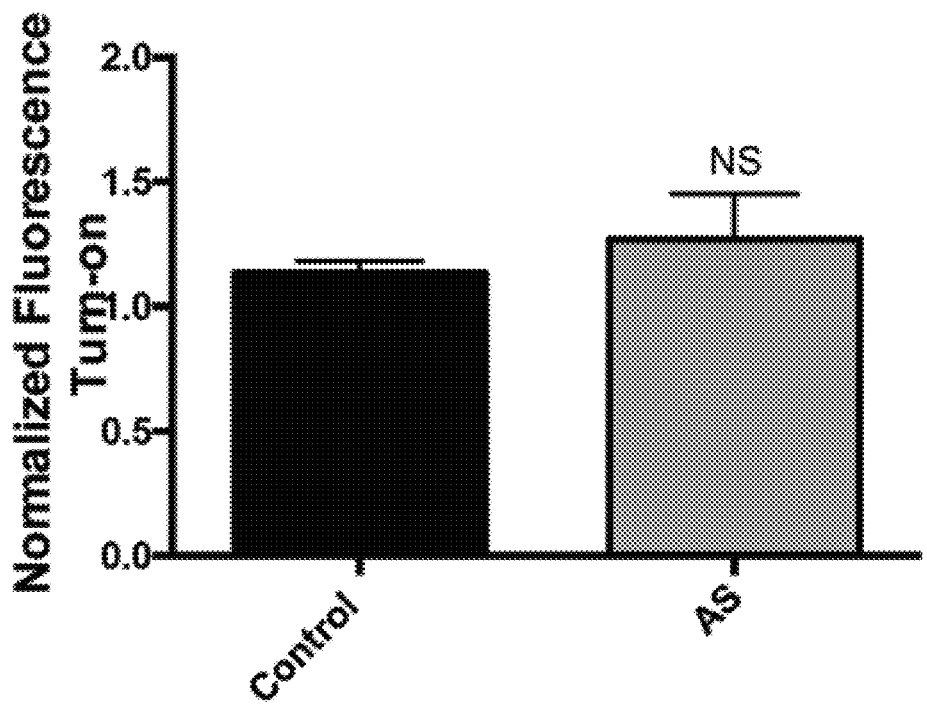
FIG. 5. The normalized fluorescence turn-on response of S-methyl NitroxylBlue treated with vehicle control (black) or Angeli's salt (100 μM) and incubated in PBS at 25° C. All data was taken 15 minutes after treatment.

Although incubating NB-2 with Angeli's salt did result in a more significant 3.5-fold turn-on response, it was surprising to find that NB-2 was not stable in aqueous media as the background enhancement at 37° C. was 1.6-fold after 10 minutes (FIG. 4). To determine whether this was due to hydrolysis or alpha-thiolactonization, a control reagent by blocking the reactivity of the thiol via methylation of NB-2 was developed. No hydrolysis was observed after incubation in aqueous media, providing compelling evidence that the release of the coumarin was indeed due to alpha-thiolactonization (FIG. 5). To address this instability issue it was sought to further stabilize the ester moiety by exploiting X . . . C=O n→π*interactions (where X=halogen) by installing an ortho-chloro substituent to give rise to NitroxyBlue-3 (NB-3) (Scheme 1a). It was reasoned this modification would be sufficient to prevent intramolecular attack by the thiol, yet would allow for cyclization of the more reactive N-hydroxysulfenamide alpha-nucleophile. Indeed, when NB-3 was treated with a vehicle control, any fluorescence enhancement was not observed, indicating the ortho-chloro substituent was sufficient to stabilize the ester from alpha-thiolactonization (FIG. 4). On the other hand, the addition of Angeli's salt resulted in a 3.6-fold turn-on response (FIG. 4).

Having established a new thiol-based HNO-responsive trigger on a commercially available coumarin scaffold, a custom HNO probe with an absorbance and emission profile in the visible spectrum was developed. Visible wavelength probes are more desirable than their UV counterparts for biological studies since visible light is less phototoxic. This led to the development of the final probe in this series, NitroxylFluor, which is based on a chlorinated hydroxymethyl fluorescein platform. Synthesis of NitroxylFluor was achieved by diallylation of fluorescein with allyl bromide to afford 1 in 37% yield. Lithium aluminum hydride reduction of the allyl ester also resulted in reduction of the xanthene moiety to give the hydroxymethyl intermediate 2 in 83% yield. Disruption of the xanthene π-system facilitated regioselective ortho, ortho-dichlorination of the resulting phenol moiety under basic conditions using sodium hypochlorite to yield 3. Of note, an exhaustive search was not tried in order to obtain the mono-chloro product since di-chlorination would likely lead to greater stabilization against alpha-lactonization. The chromophore was reestablished via chloranil oxidation to afford 4, which was subsequently capped using a tritylated 2-mercaptoisobutyric acid building block under Steglich coupling conditions to give 5 in 60% yield over 2-steps. The O-allyl functionality was removed under Tsuji-Trost deallylation conditions to afford 6 in near quantitative yields. Finally, the trityl protecting group was removed under acidic conditions to give NitroxylFluor in 13% yield (Scheme 2).

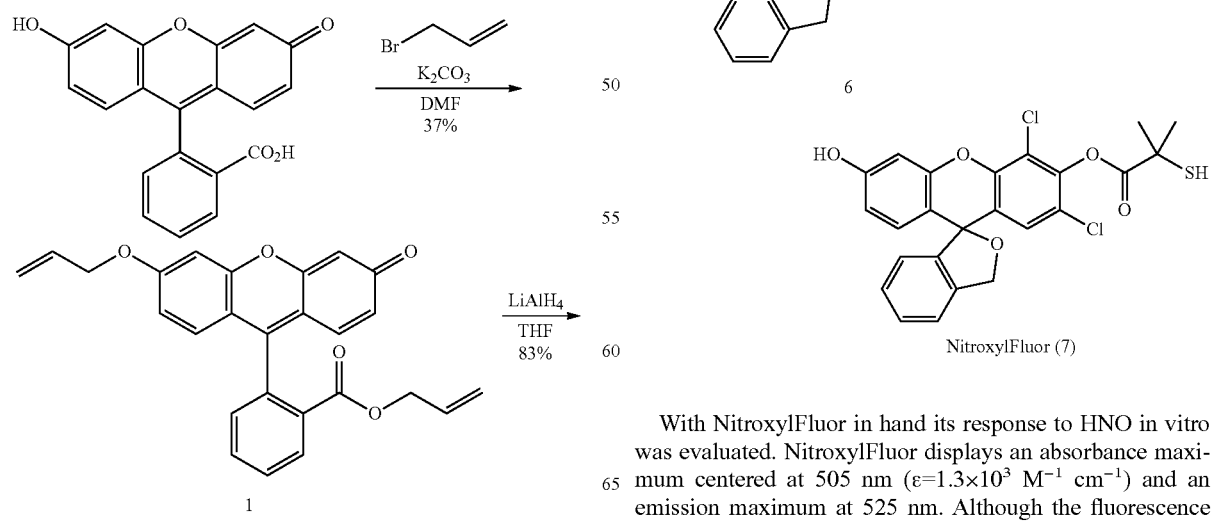

Scheme 2. Synthesis of NitroxylFluor

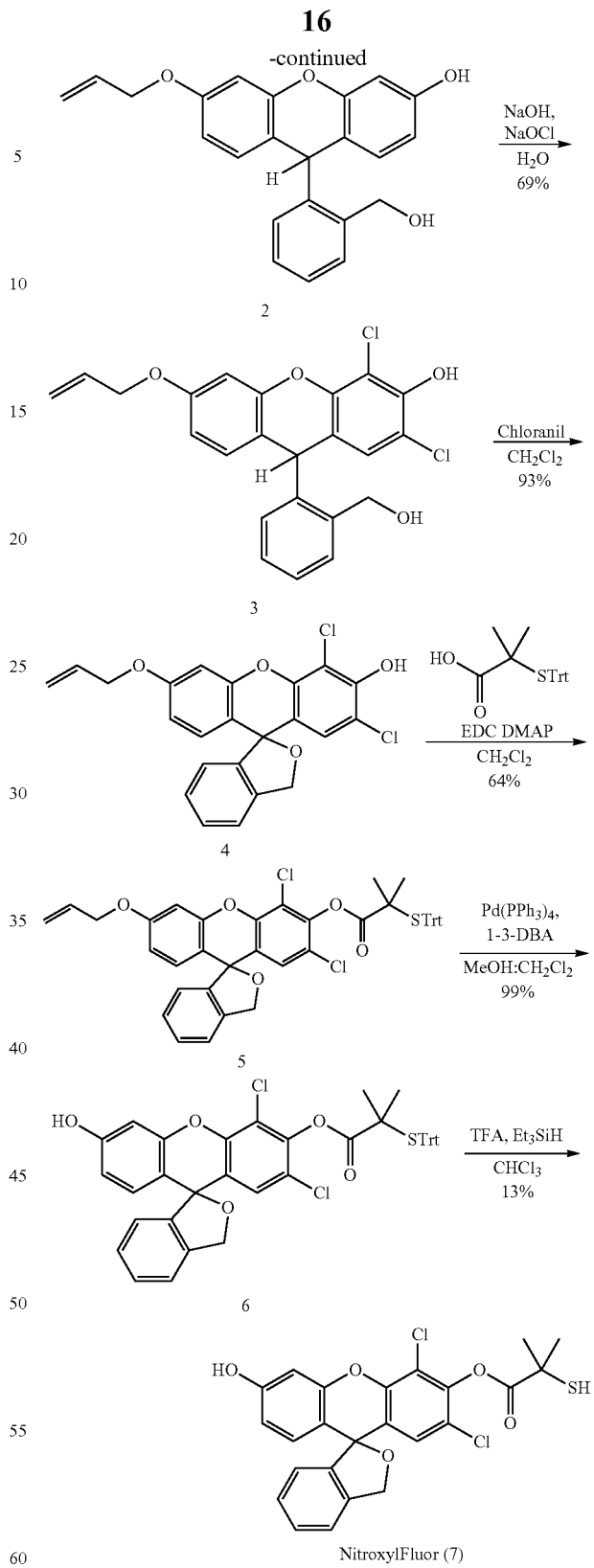

Figure 2:
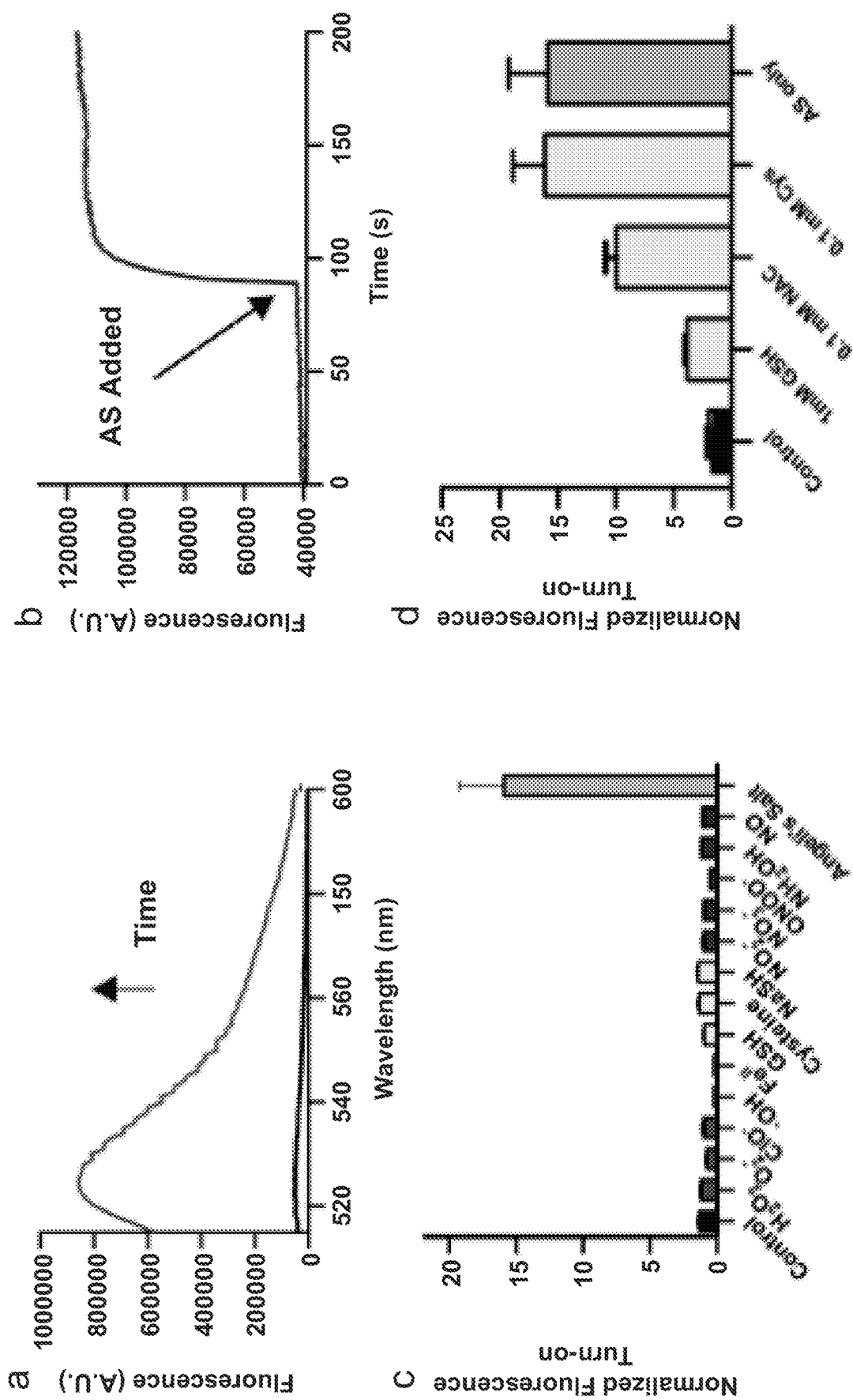
FIG. 2. a) Fluorescence spectra of NitroxylFluor (2 μM) upon addition of AS (100 μM). b) Fluorescence kinetic trace of NitroxylFluor upon addition of 1 mM Angeli's salt, arrow indicates time of addition. c) Response of NitroxylFluor to various reactive oxygen, sulfur, and nitrogen species at concentrations of 100 μM (GSH was tested at 1 mM). Measurements were taken 15 minutes into treatment. d) Competition assays against various thiols. Control indicates no addition of Angeli's salt. Statistics are compared to the control. *, $p<0.05$; ***, $p<0.001$; $p<0.0001$. (n=3).

With NitroxylFluor in hand its response to HNO in vitro was evaluated. NitroxylFluor displays an absorbance maximum centered at 505 nm ($\varepsilon = 1.3 \times 10^3$ M$^{-1}$ cm$^{-1}$) and an emission maximum at 525 nm. Although the fluorescence was initially attenuated, reaction with HNO afforded a 16-fold fluorescent turn-on response in a matter of seconds (FIG. 2a and FIG. 2b). Given the rapid reaction of HNO with thiols, it was speculated that the rate-limiting step is not formation of the N-hydroxysulfenamide intermediate, but rather cyclization. Having established excellent responsiveness to HNO, attention was turned to determining the selectivity profile of the trigger. In particular, NitroxylFluor was treated with various oxidants, including $H_2O_2$ because it is known that thiols can be oxidized to sulfenic acids (RSOH), sulfinic acids ($RSO_2H$), and sulfonic acids ($RSO_3H$), which can potentially cyclize to release the dye. However, cross-reactivity with any of the oxidants tested was not observed (FIG. 2c). Likewise, when NitroxylFluor was incubated with various reactive sulfur species (e.g., $H_2S$) and reactivate nitrogen species (e.g., NO) there was no change in fluorescence after a 15-minute incubation at 37° C. (FIG. 2c). Taken together this demonstrates high selectivity of the trigger for HNO.

Figure 6:
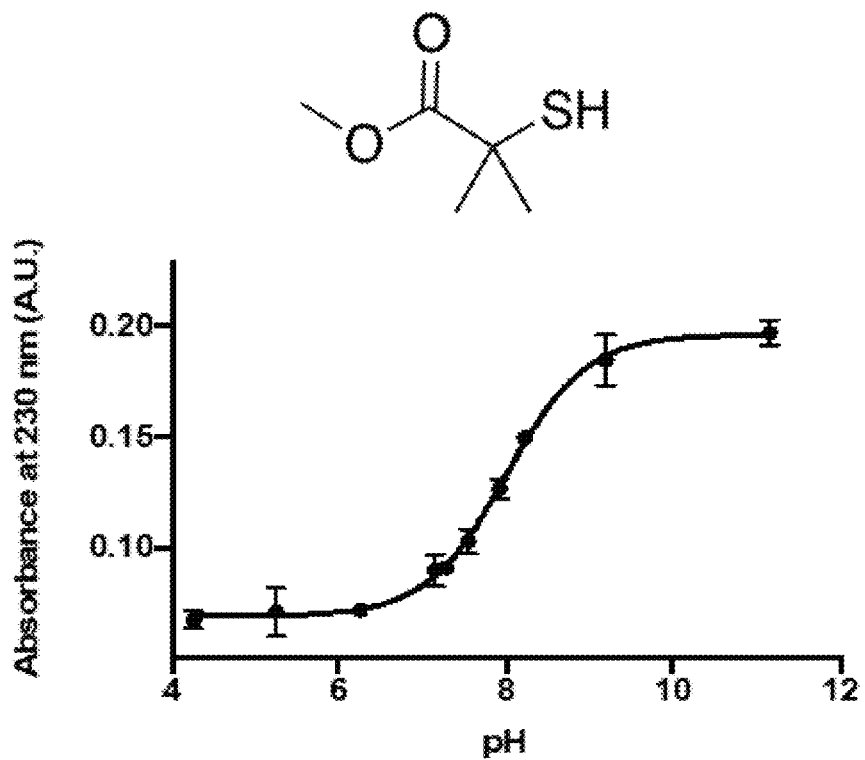
FIG. 6. pH profile of compound 16 ($pK_a$=8.01). Assay was completed by measuring the absorbance at 230 nm as described by Tajc et al. (J Am Chem Soc 2004, 126, 10508). Each reading was taken in triplicate and averaged in the respective pH Britton-Robinson Universal Buffer.

Next was evaluated whether NitroxylFluor possessed requisite reactivity to compete against biologically relevant thiols for HNO. In these experiments, 10 μM solutions of NitroxylFluor and various thiols such as L-cysteine (100 μM), N-acetyl-L-cysteine (100 μM), and GSH (1 mM) was treated with Angeli's salt (200 μM) (FIG. 2d). In the case of L-cysteine, the fluorescence response was not attenuated (16.2-fold increase) indicating NitroxylFluor was the more reactive species. Similarly, competition with N-acetyl-L-cysteine resulted in a 9.8-fold fluorescence enhancement. GSH on the other hand is highly abundant in cells (millimolar concentrations) and reacts rapidly with HNO ($k=2\times 10^6 M^{-1} s^{-1}$). Thus, interference from GSH presents a significant challenge for any HNO detection strategy. Even in the presence of 1 mM GSH, treatment of NitroxylFluor with Angeli's salt still gave rise to a 3.9-fold fluorescent turn-on response. To determine the origin of why NitroxylFluor can function in the presence of a large excess GSH, a control compound was synthesized where the dye was replaced with a methoxy nucleofuge (Scheme 7). It was not anticipated that this would significantly alter the pKa of the thiol. However, the poor leaving group ability of the methoxy suppresses alpha-thiolactonization, which allowed us to measure a pKa value of 8.01 by UV/vis spectroscopy (FIG. 6). In comparison, the reported pKa value of GSH is 9.42. The lower pKa of the probe renders it more reactive towards HNO and presents a unique opportunity to further tune reactivity by simply modulating the pKa of thiol-based triggers.

Figure 3:
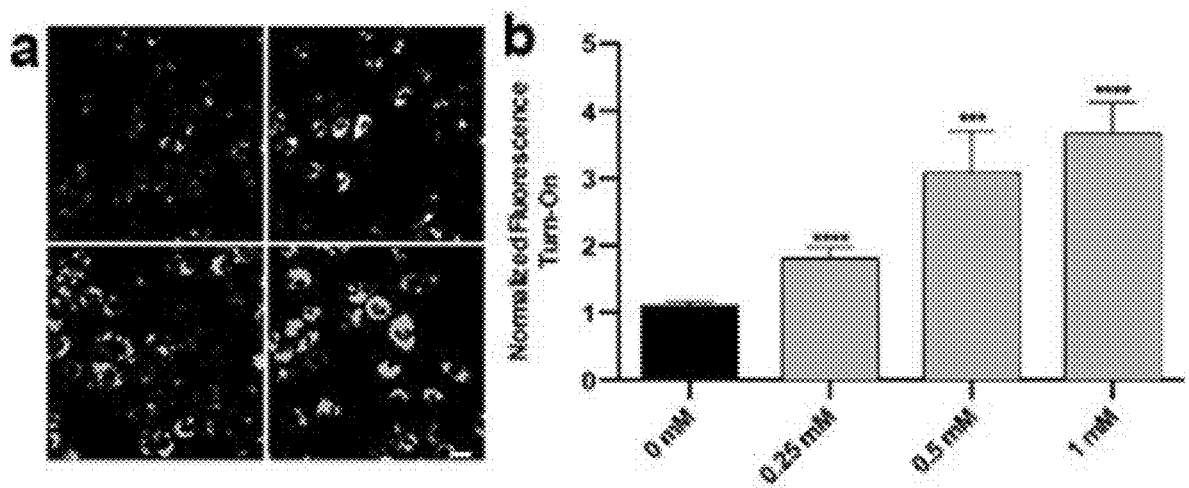
FIG. 3. Confocal microscopy images acquired by irradiation of MDA-MB-231 cells treated with 0 μM (vehicle control), 250 μM, 500 μM, 1000 μM Angeli's salt for 15 mins at 25° C. with a 488 nm laser. Images taken through a 40× oil immersion objective. Scale bar represents 20 μm. b) Quantification of imaging data. *, $p<0.05$; ***, $p<0.001$; $p<0.0001$.
Figure 8:
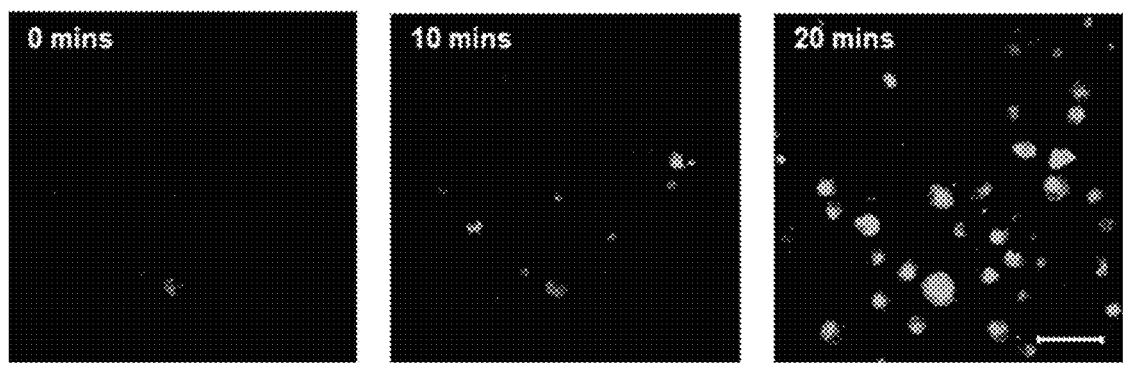
FIG. 8. Representative time course imaging of MDA-MB-231 cells stained with 4 μM NitroxylFluor for 15 minutes followed by replacement with fresh PBS with no probe. Angeli's salt (200 μM) was added 5 minutes after PBS was replaced. Images were taken through a 40× oil immersion objective at 0, 10, and 20 mins after AS addition at 25° C. via irradiation with a 488 nm laser. Scale bar represents 20 μm.
Figure 9:
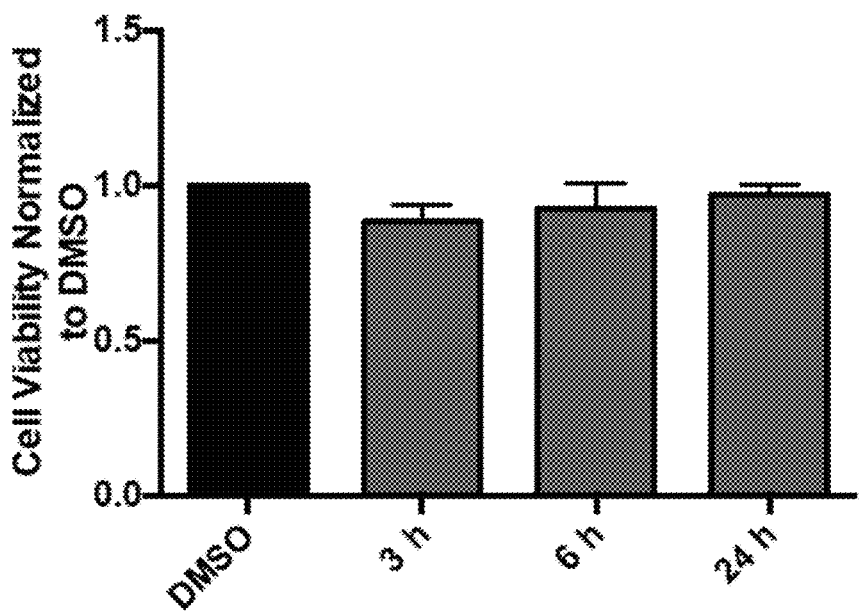
FIG. 9. MTT assay to determine the cytotoxicity of NitroxylFluor at 4 μM over 3, 6, and 24 hours. Detailed protocol available on page 3 of this supporting information document. No time point has significant difference from the DMSO control (n=3, error bars are standard deviations).
Figure 10:
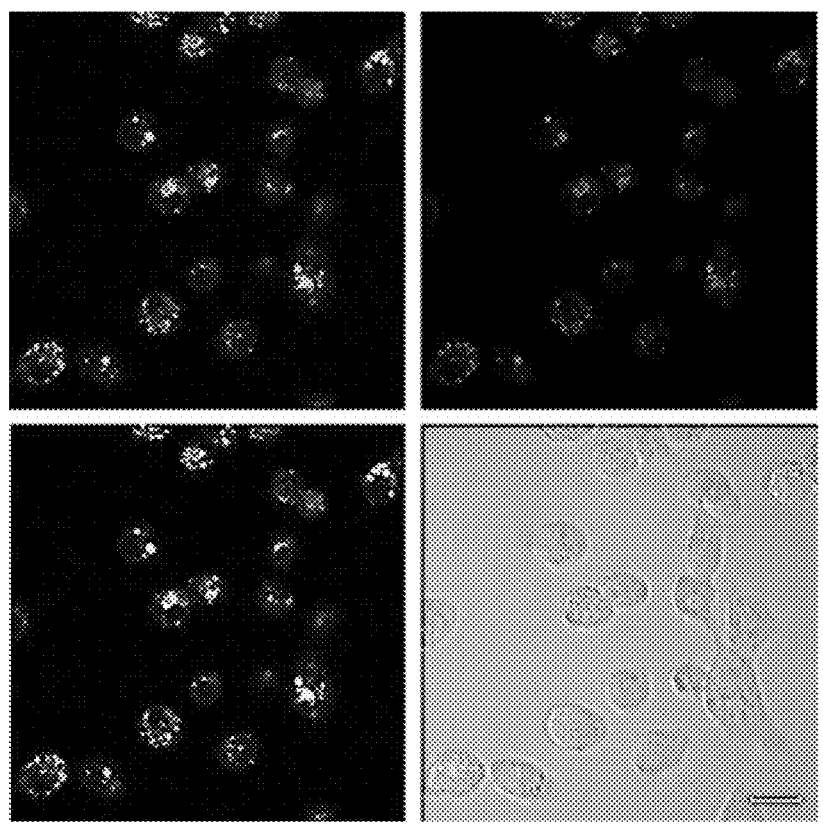
FIG. 10. Co-incubation of NitroxylFluor after Angeli's salt treatment (250 μM) with LysoTracker® Red for roughly 5 minutes at 25° C. Top left: Green channel representing only NitroxylFluor. Top right: Red channel representing only LysoTracker® Red. Bottom left: Merge of green and red channels where yellow signifies fluorescence overlap between NitroxylFluor and LysoTracker® Red. Bottom right: Bright field image of the cells incubated. Scale bar represents 50 μm. Pearson's Coefficient=0.932±0.01 (n=5).
Figure 11:
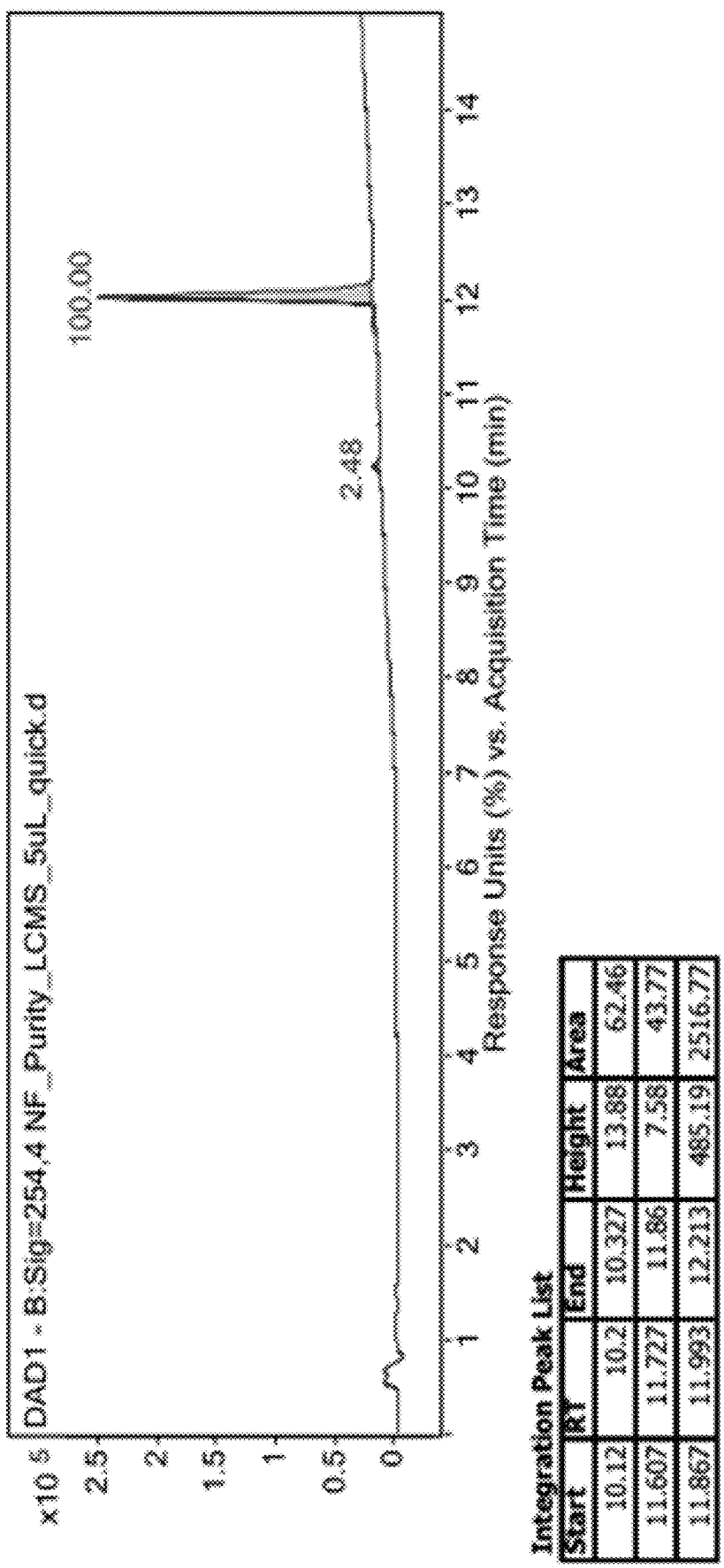
FIG. 11. LC trace of NitroxylFluor to access purity. Calculated purity is 95.95%. The peak that appears at 10.2 mins corresponds to the disulfide of the probe that forms upon sitting in acetonitrile.

After demonstrating excellent responsiveness to HNO, exceptional selectivity over a range of biological analytes, and effective competition with thiols, the ability of NitroxylFluor to visualize HNO was tested in living cells. Specifically, MDA-MB-231 cells, a human breast adenocarcinoma cell line, was stained with NitroxylFluor for 15 minutes before removing the probe solution and replacing with fresh media. Addition of Angeli's salt at various concentrations (250 μM to 1000 μM) resulted in a dose-dependent fluorescence turn-on response after 15 mins (FIG. 3a and FIG. 3b). A statistically significant enhancement was observed even for the lowest Angeli's salt concentration. Also performed was time-lapse imaging by treating NitroxylFluor stained cells with 500 μM Angeli's salt and recorded images every 1 min after addition for 20 mins. A gradual increase in the fluorescence during this time course was noted. Representative images at 0, 10, and 20 mins are shown in FIG. 8. The cytotoxicity of NitroxylFluor was also evaluated by performing a MTT assay when MDA-MB-231 cells were stained with 10 μM probe for 3, 6, and 24 h. Cytotoxicity at any time point was not observe (FIG. 9). The subcellular localization of NitroxylFluor in MDA-MB-231 cells appeared to be lysosomal. This was confirmed by using a commercial lysosome stain (LysoTracker Red) and significant overlap in signal was observed with a Pearson's Coefficient of 0.932±0.01 (FIG. 10).

In conclusion, the known reactivity of thiols with HNO was harnessed to develop a novel HNO-reactive trigger. Physical organic phenomena was then called upon to improve upon this reactivity to develop a probe that competes with the native chemistry, even when known scavengers are in excess. In doing this, a selective fluorescent probe for HNO was created that avoids inefficient by-products and the lack of selectivity suffered by previously reported technologies. Results indicate that the cyclization of the trigger outcompetes foreseeable side reactions. Owing to the culmination of this work, it is predicted that this technology will allow the study of HNO with enhanced rate and selectivity to elucidate its biological roles and pharmacological potential.

Pharmaceutical Formulations

The compounds described herein can be used to prepare pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, or subcutaneous routes.

The compounds described herein may be systemically administered in combination with a pharmaceutically acceptable vehicle, such as an inert diluent or an assimilable edible carrier. For oral administration, compounds can be enclosed in hard- or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. General Methods

Materials. 3-(4,5-Dimethylthiazol-2-yl)-2,5-diphenyltetrazolium bromide (MTT), dichloromethane, isoamyl nitrite, and triethylamine were purchased from Acros Organic. 1,3-Dimethylbarbituric acid was purchased from AK Scientific. Allyl bromide and sodium hypochlorite (14.5% available chlorine in water) were purchased from Alfa Aesar. Sodium acetate was purchased from Amersco. All deuterated solvents were purchased from Cambridge Isotope Laboratories. Methylamine hexamethylene methylamine NONOate (MAHMA-NONOate) and sodium α-oxyhyponitrite (Angeli's salt) were purchased from Cayman Chemicals. Chloroform, diethyl ether, ethyl acetate, phosphate saline buffer (Corning), potassium phosphate dibasic, potassium phosphate monobasic, sodium bicarbonate, sodium chloride, and toluene were purchased from Fisher Scientific. LysoTracker® Red, was purchased from Life Technologies. Acetonitrile, anhydrous methanol, concentrated hydrochloric acid, hydrogen peroxide (30% v/v) and sodium hydroxide were purchased from Macron Fine Chemicals. 4-Dimethylaminopyridine, N-(3-dimethylaminopropyl)-N'-ethylcarbodiimide hydrochloride, potassium carbonate, potassium hydroxide, sodium sulfate (anhydrous), tetrakis(triphenylphosphine)palladium(0), triphenylmethanol and were purchased from Oakwood Chemicals. Ammonium iron sulfate (Mohr's salt), anhydrous dichloromethane, anhydrous N,N-dimethylformamide, anhydrous tetrahydrofuran, Celite 545, dithiodiglycolic acid, potassium superoxide, sodium nitrite, thiourea, and trifluoroacetic acid were purchased from Sigma Aldrich.

Instruments.

$^1$H and $^{13}$C NMRs were acquired on Varian 400, Varian 500, or Carver B500 spectrometers. Spectra were visualized and analyzed using MestReNova (version 10.0). High-resolution mass spectra were acquired with a Waters Q-TOF Ultima ESI mass spectrometer and a Waters Synapt G2-Si ESI/LC-MS mass spectrometer. Ultraviolet-visible (UV-Vis) measurements or spectra were recorded on a Cary 60 spectrometer or SpectraMax M2 plate reader (Molecular Devices). Fluorescence spectra were acquired on a QuantaMaster-400 scanning spectrofluorometer with micro fluorescence quartz cuvettes (Science Outlet). Fluorescence data was taken with a slit width of 0.5 mm. Cellular imaging was performed on a Zeiss LSM 700 Confocal Microscope and analyzed with Fiji software. All other data analysis was performed using GraphPad Prism (version 6.0). Mettler Toledo Seven Compact pH meter was used for pH measurements.

Cell Culture.

MDA-MB-231 adenocarcinoma cells were acquired from Prof. David J. Shapiro (Biochemistry, UIUC). Cells were cultured in phenol-red free Dulbecco's modified eagle medium (DMEM, Corning) supplemented with 10% fetal bovine serum (FBS, Sigma Aldrich), and 1% penicillin/streptomycin (Corning). Cells were incubated at 37° C. with 5% $CO_2$. Experiments were performed in 8-well chambered cover glasses (Lab-Tek, Thermo Scientific).

Cell Imaging Procedure.

An 8-well chambered cover glass was seeded with 0.4 mL of the above-mentioned cells at a density of 200,000 cells/mL. Cells were imaged at roughly 80% confluency (24 hours after seeding). Media was removed from each well and cells were washed with 200 µL PBS. The PBS was removed from the wells and replaced with 198 µL. 2 µL of 200 µM NitroxylFluor in PBS was added and gently stirred before being allowed to incubate at 37° C. with 5% $CO_2$ for 15 minutes. PBS was then removed from the wells and replaced with 195 µL, 190 µL, or 180 µL PBS. The remaining volume to 200 µL was filled with 10 mM Angeli's salt in 10 mM KOH (or 10 mM KOH in the vehicle control) to give final concentrations of 0.250 mM, 0.500 mM, or 1 mM Angeli's salt. Cells were again allowed to incubate for 15 minutes incubate at 37° C. with 5% $CO_2$. 3-5 images of each well were taken and their mean fluorescence (as reported by ImageJ) was averaged to give an average value for each well. 5 biological replicates over 3 different passage numbers were conducted. Average values of each well (biological replicate) were subjected to the statistical analysis demonstrated in FIG. 4.

Reagent Preparation for In Vitro Assays.

Angeli's salt was stored at −20° C. Stocks of Angeli's salt were added as a 10 mM solution in 10 mM KOH (for stability). Hydrogen peroxide was added as a 10 mM stock solution prepared by diluting 30% hydrogen peroxide in deionized water. Superoxide was added as a 1 mM stock solution of potassium superoxide in DMSO (for stability). Hypochlorite was added as a 10 mM stock solution prepared by diluting 30% sodium hypochlorite in deionized water.

Hydroxyl radical was prepared by first preparing a 10 mM solution of Mohr's Salt ($Fe(NH_4)_2(SO_4)_2 \cdot 6H_2O$) in 0.1 M HCl which was degassed by bubbling nitrogen gas for 20 minutes through the solution. A solution of the probe was made in buffer and degassed and the initial reading was taken. 10 µL of 10 mM Hydrogen Peroxide and Mohr's salt solution giving a final volume of 1 mL (100 µM hydroxyl radical) were added and allowed to incubate at 37° C. for the duration of the selectivity assay with a septum on the cuvette. Iron(II) was prepared via the same procedure as hydroxyl radical only hydrogen peroxide was not added. Glutathione was added as a 100 mM stock solution in PBS buffer. Cysteine was added as a 10 mM stock solution in PBS buffer. NaSH was added as a 10 mM stock solution in deionized water. Nitrite was added as a 10 mM stock solution of sodium nitrite in deionized water. Nitrate was added as a 10 mM stock solution of sodium nitrate in deionized water.

Peroxynitrite was prepared by dissolving 0.24 mL 30% hydrogen peroxide and 0.27 mL n-amyl nitrite in 4.5 mL 0.55 M KOH and 5 mL isopropyl alcohol. This was stirred at room temperature for 15 minutes and transferred to a separatory funnel to be washed with 2×20 mL $CH_2Cl_2$. A scoop of $MnO_2$ was added to the bright yellow aqueous layer and stirred for 5 minutes. This was filtered through a Pasteur pipette fitted with a plug of cotton and Celite. The resulting solution was kept on ice and the concentration of the stock was determined by measuring absorbance at 302 nm ($\varepsilon$=1670 $M^{-1}$ $s^{-1}$). This solution was added directly to the assay solution to give a 100 µM final concentration of peroxynitrite. Hydroxylamine was added as a 10 mM stock solution of hydroxylamine in deionized water. Nitric oxide was prepared with MAHMA NONOate. MAHMA NONOate was stored at 80° C. Stocks of MAHMA NONOate were added as a 10 mM solution in 10 mM KOH (for stability).

MTT Cytotoxicity Assay.

Figure 7:
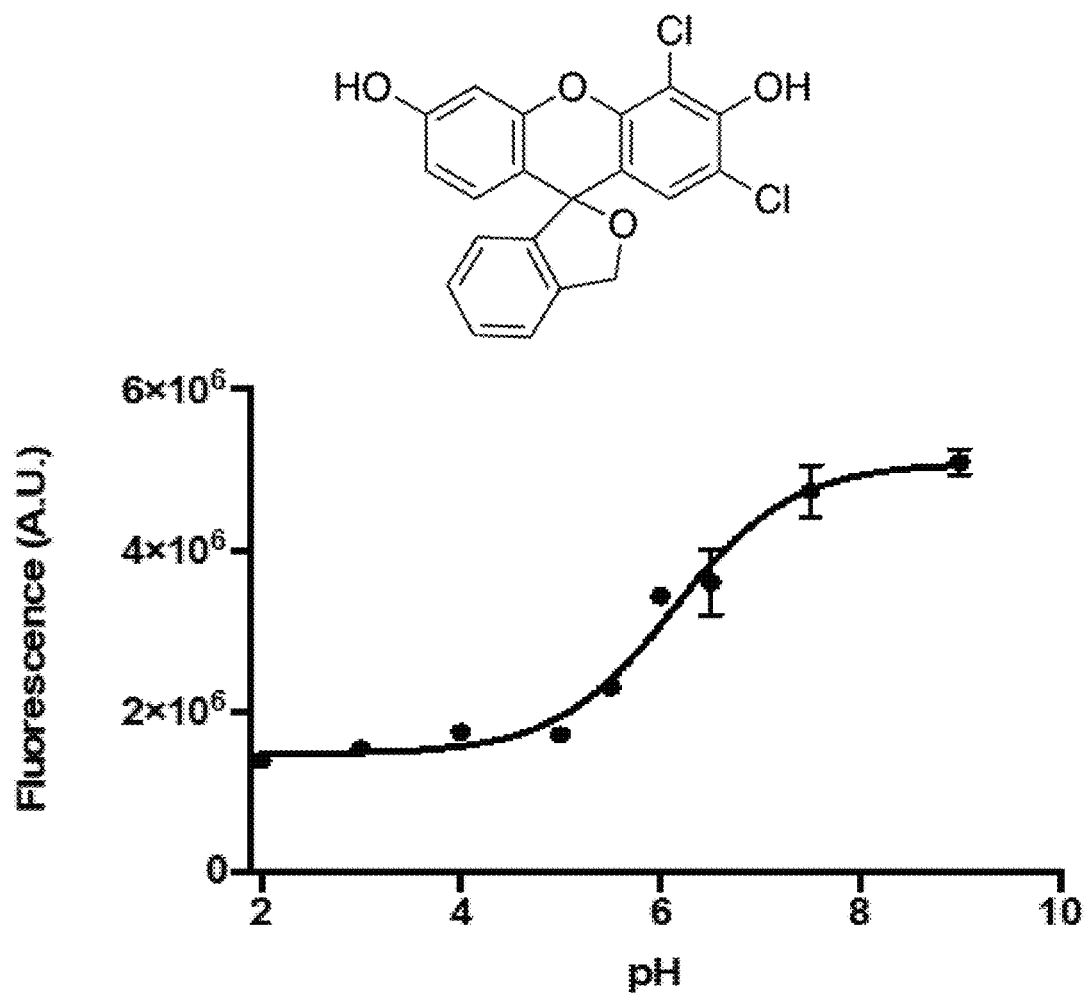
FIG. 7. pH profile of fully reacted NitroxylFluor product ($pK_a$=6.13). Assay was completed by measuring fluorescence at 525 nm when excited at 505 nm. Each reading was taken in triplicate and averaged in the respective pH Britton-Robinson Universal Buffer.

A 96-well plate was seeded with 20,000 cells per well (200 µL of 150,000 cells/mL) and incubated at 37° C. with 5% $CO_2$ for 24 h (~70% confluent). Media was removed and fresh serum-free DMEM media (199 µM) was applied followed by addition of 1 µM vehicle control (DMSO) or NitroxylFluor for a final concentration of 4 µM. After 3, 6, and 24 h the media was removed and replaced with 200 µM 20:1 mixture of FBS-free DMEM and (3-(4,5-dimethylthiazol-2-yl)-2,5-diphenyl-tetrazolium bromide (MTT, 5 mg/mL stock in PBS). The cells were incubated for 4 h under the same conditions and then the medium was removed and replaced with DMSO (100 μM/well). The absorbance of each well was recorded at 555 nm on a microplate reader. Viability was calculated by the absorbance relative to the vehicle control. Results pictured in FIG. 7.

Example 2. Synthesis Procedures

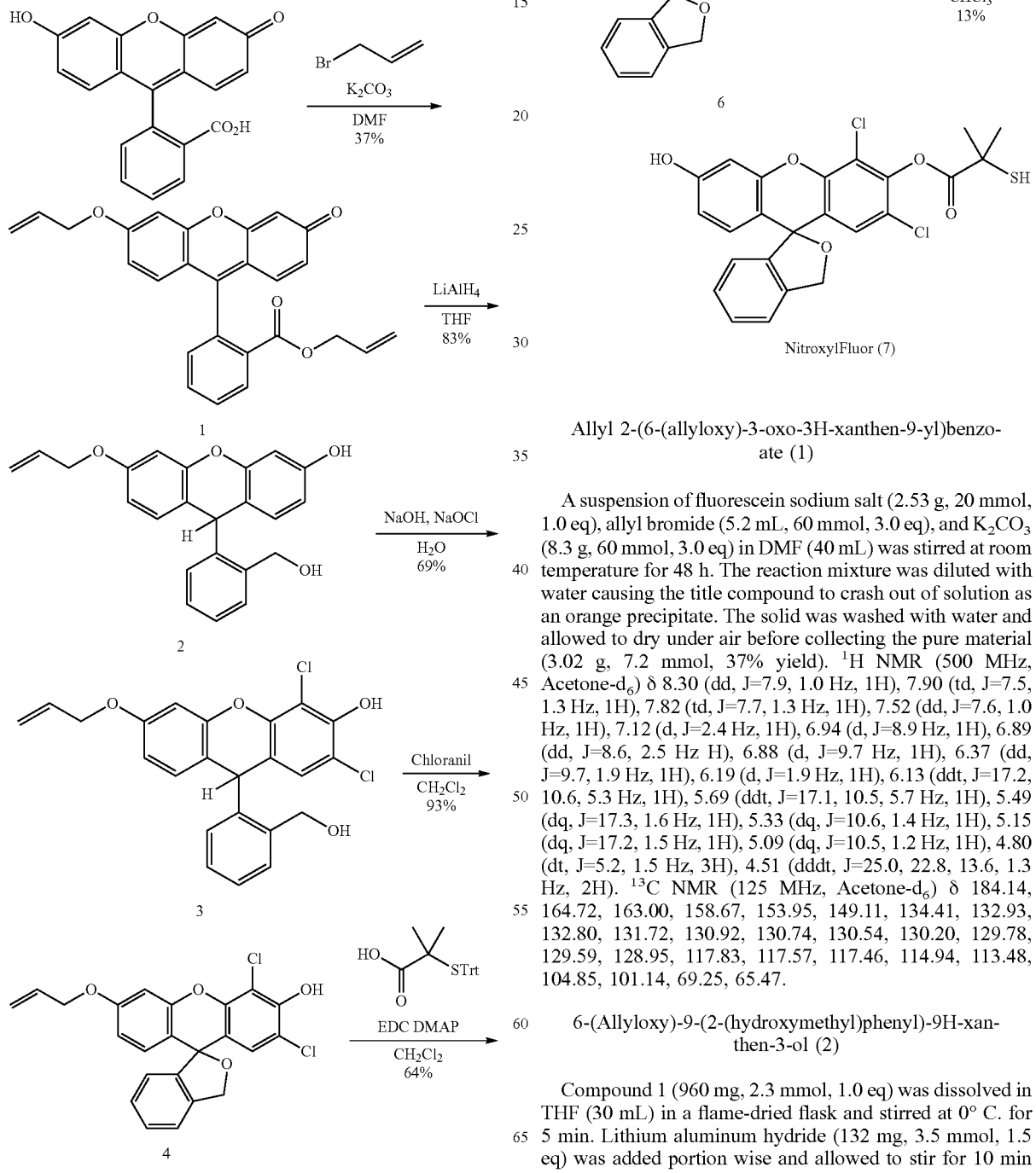

Allyl 2-(6-(allyloxy)-3-oxo-3H-xanthen-9-yl)benzoate (1)

A suspension of fluorescein sodium salt (2.53 g, 20 mmol, 1.0 eq), allyl bromide (5.2 mL, 60 mmol, 3.0 eq), and $K_2CO_3$ (8.3 g, 60 mmol, 3.0 eq) in DMF (40 mL) was stirred at room temperature for 48 h. The reaction mixture was diluted with water causing the title compound to crash out of solution as an orange precipitate. The solid was washed with water and allowed to dry under air before collecting the pure material (3.02 g, 7.2 mmol, 37% yield). $^1$H NMR (500 MHz, Acetone-$d_6$) δ 8.30 (dd, J=7.9, 1.0 Hz, 1H), 7.90 (td, J=7.5, 1.3 Hz, 1H), 7.82 (td, J=7.7, 1.3 Hz, 1H), 7.52 (dd, J=7.6, 1.0 Hz, 1H), 7.12 (d, J=2.4 Hz, 1H), 6.94 (d, J=8.9 Hz, 1H), 6.89 (dd, J=8.6, 2.5 Hz H), 6.88 (d, J=9.7 Hz, 1H), 6.37 (dd, J=9.7, 1.9 Hz, 1H), 6.19 (d, J=1.9 Hz, 1H), 6.13 (ddt, J=17.2, 10.6, 5.3 Hz, 1H), 5.69 (ddt, J=17.1, 10.5, 5.7 Hz, 1H), 5.49 (dq, J=17.3, 1.6 Hz, 1H), 5.33 (dq, J=10.6, 1.4 Hz, 1H), 5.15 (dq, J=17.2, 1.5 Hz, 1H), 5.09 (dq, J=10.5, 1.2 Hz, 1H), 4.80 (dt, J=5.2, 1.5 Hz, 3H), 4.51 (dddt, J=25.0, 22.8, 13.6, 1.3 Hz, 2H). $^{13}$C NMR (125 MHz, Acetone-$d_6$) δ 184.14, 164.72, 163.00, 158.67, 153.95, 149.11, 134.41, 132.93, 132.80, 131.72, 130.92, 130.74, 130.54, 130.20, 129.78, 129.59, 128.95, 117.83, 117.57, 117.46, 114.94, 113.48, 104.85, 101.14, 69.25, 65.47.

6-(Allyloxy)-9-(2-(hydroxymethyl)phenyl)-9H-xanthen-3-ol (2)

Compound 1 (960 mg, 2.3 mmol, 1.0 eq) was dissolved in THF (30 mL) in a flame-dried flask and stirred at 0° C. for 5 min. Lithium aluminum hydride (132 mg, 3.5 mmol, 1.5 eq) was added portion wise and allowed to stir for 10 min before the solution warmed to room temperature. After 40 min, the reaction was quenched with 1 M HCl on ice. The solution was concentrated leaving only the aqueous layer which was extracted with CH$_2$Cl$_2$. The organic layer was washed with brine (3×) then dried over Na$_2$SO$_4$. The crude mixture was purified by silica gel chromatography with 1:39 v/v MeOH/CH$_2$Cl$_2$ to yield the title compound as a white, flaky solid (650 mg, 1.8 mmol, 77% yield) $^1$H NMR (500 MHz, Acetone-d$_6$) δ 8.60 (s, 1H), 7.50 (s, 1H), 7.18 (s, 2H), 7.11 (s, 1H), 6.97 (d, J=8.3 Hz, 1H), 6.92 (d, J=8.2 Hz, 1H), 6.71 (d, J=8.8 Hz, 2H), 6.63-6.49 (m, 2H), 6.17-5.98 (m, 1H), 5.65 (s, 1H), 5.43 (d, J=17.2 Hz, 1H), 5.26 (d, J=10.3 Hz, 1H), 4.86 (s, 2H), 4.54 (s, 2H). $^{13}$C NMR (125 MHz, Acetone-d$_6$) δ 158.33, 157.02, 151.40, 145.69, 138.50, 133.68, 130.70, 130.65, 130.62, 128.29, 127.97, 126.30, 117.09, 116.83, 115.83, 111.25, 110.62, 102.68, 101.81, 68.62, 62.28, 54.14, 38.28.

6-(Allyloxy)-2,4-dichloro-9-(2-(hydroxymethyl)phenyl)-9H-xanthen-3-ol (3)

5.25% wt/wt NaOCl (1 mL, 0.75 mmol, 2.5 eq) was added to a solution of compound 2 (100 mg, 0.30 mmol, 1.0 eq) in 0.1 M NaOH (12 mL). The resultant solution was stirred at room temperature for 3 h. The reaction was quenched with 0.1 M HCl, then extracted with EtOAc (2×). The resulting organic layer was washed with brine (2×) and the dried over Na$_2$SO$_4$. The crude mixture was purified by a silica gel column chromatography with a gradient of 1:39 to 1:9 v/v MeOH/CH$_2$Cl$_2$ giving the title compound as a pale orange solid (60.0 mg, 0.02 mmol, 47% yield). $^1$H NMR (500 MHz, Acetone-d$_6$) δ 7.49-7.42 (m, 1H), 7.23-7.16 (m, 2H), 7.09 (s, 1H), 7.07-7.02 (m, 1H), 6.96 (d, J=8.6 Hz, 1H), 6.79 (d, J=2.5 Hz, 1H), 6.62 (dd, J=8.6, 2.5 Hz, 1H), 6.07 (ddt, J=15.8, 10.4, 5.1 Hz, 1H), 5.72 (s, 1H), 5.43 (dq, J=17.2, 1.6 Hz, 1H), 5.26 (dq, J=10.6, 1.3 Hz, 2H), 4.90 (d, J=12.7 Hz, 1H), 4.83 (d, J=12.7 Hz, 1H), 4.58 (d, J=5.2 Hz, 2H). $^{13}$C NMR (125 MHz, Acetone-d$_6$) δ 158.50, 150.54, 148.57, 146.17, 145.15, 138.53, 133.56, 130.55, 130.49, 128.74, 128.32, 128.06, 126.62, 118.27, 116.75, 116.21, 115.53, 111.65, 109.57, 101.84, 68.67, 62.47, 38.02.

6'-(Allyloxy)-2',4'-dichloro-3H-spiro[isobenzofuran-1,9'-xanthen]-3'-ol (4)

A solution of compound 3 (550 mg, 1.3 mmol, 1.0 eq) and chloranil (378 mg, 1.54 mmol, 1.1 eq) in CH$_2$Cl$_2$ (40 mL) was stirred at room temperature for 7 h. The crude mixture was concentrated and purified via silica gel column chromatography using 7:3 v/v EtOAc/Hexanes to yield the title compound as an orange solid (500 mg, 1.2 mmol, 93% yield). $^1$H NMR (500 MHz, Acetone-d$_6$) δ 7.49 (s, 1H), 7.43 (t, J=7.1 Hz, 1H), 7.32 (t, J=7.2 Hz, 2H), 6.97 (s, 1H), 6.96 (d, J=9.5 Hz, 1H), 6.92 (d, J=7.6 Hz, 2H), 6.90 (d, J=2.5 Hz, 2H), 6.76 (dd, J=8.7, 2.5 Hz, 2H), 6.10 (ddt, J=17.2, 10.5, 5.2 Hz, 2H), 5.45 (dq, J=17.3, 1.6 Hz, 2H), 5.40 (d, J=12.7 Hz, 2H), 5.35 (d, J=12.6 Hz, 2H), 5.28 (dq, J=10.6, 1.5 Hz, 2H), 4.67 (dt, J=5.1, 1.4 Hz, 5H). $^{13}$C NMR (125 MHz, Acetone-d$_6$) δ 205.35, 159.53, 150.50, 149.69, 145.88, 144.94, 138.88, 133.40, 129.71, 128.45, 128.41, 127.05, 123.28, 121.20, 119.09, 117.25, 116.78, 116.15, 112.51, 109.09, 101.13, 82.96, 72.33, 68.75.

6'-Allyloxy-2',4'-dichloro-3H-spiro[isobenzofuran-1,9'-xanthen]-3'-yl 2-methyl-2-(tritylthio)propanoate (5)

A solution of compound 4 (34.5 mg, 0.08 mmol, 1.0 eq), compound 9 (32.19 mg, 0.09 mmol, 1.1 eq), EDC hydrochloride (33.74 mg, 0.18 mmol, 2.2 eq), and DMAP (3.91 mg, 0.03 mmol, 0.4 eq) in CH$_2$Cl$_2$ (5 mL) was stirred at room temperature overnight. The resulting mixture was washed with brine (23). The organic fraction was then dried over Na$_2$SO$_4$ and concentrated under reduced pressure. The crude residue was purified by silica gel column chromatography in 1:9 v/v EtOAc/Hexanes to yield the product as an off-white solid (39.7 mg, 0.05 mmol, 64% yield). $^1$H NMR (500 MHz, Acetone-d$_6$) δ 7.57 (d, J=7.3 Hz, 6H), 7.52 (d, J=7.6 Hz, 1H), 7.45 (td, J=8.3, 7.5, 0.8 Hz, 1H), 7.35 (t, J=7.6 Hz, 6H), 7.28 (t, J=7.3 Hz, 3H), 7.18 (s, 1H), 7.02 (d, J=8.8 Hz, 1H), 6.97 (d, J=7.6 Hz, 1H), 6.94 (d, J=2.5 Hz, 1H), 6.80 (dd, J=8.8, 2.5 Hz, 1H), 6.10 (ddt, J=17.2, 10.5, 5.2 Hz, 1H), 5.48 (d, J=13.0 Hz, 1H), 5.47 (dq, J=17.3, 1.7 Hz, 1H), 5.43 (dq, J=13.0, 1.5 Hz, 1H), 5.28 (d, J=12.1 Hz, 1H), 4.67 (dt, J=5.1, 1.5 Hz, 1H), 1.37 (s, 6H). $^{13}$C NMR (125 MHz, Acetone-d$_6$) δ 169.92, 159.72, 150.27, 145.87, 144.65, 144.22, 138.68, 133.33, 130.27, 129.65, 128.68, 128.61, 127.79, 127.75, 127.40, 127.01, 125.81, 123.27, 122.15, 121.35, 116.88, 112.94, 101.21, 83.92, 82.88, 72.83, 70.43, 68.81, 52.93, 26.49.

2',4'-Dichloro-6'-hydroxy-3H-spiro[isobenzofuran-1,9'-xanthen]-3'-yl 2-methyl-2-(tritylthio)propanoate (6)

A solution of compound 5 (216.0 mg, 0.28 mmol, 1.0 eq) in CH$_2$Cl$_2$ (15.5 mL) was prepared in a flame-dried round-bottom flask. To the solution were added Pd(PPh$_3$)$_4$ (32.4 mg, 0.03 mmol, 0.1 eq) and 1,3-dimethylbarbituric acid (717.3 mg, 5.60 mmol, 20 eq). Anhydrous MeOH (15.5 mL) degassed by bubbling nitrogen gas and sonicating for 20 min was added to the solution and allowed to stir at room temperature overnight. The reaction was concentrated and purified via silica gel column chromatography with 1:4 v/v EtOAc/Hexanes to give the pure product as an off-white solid (202.4 mg, 0.28 mmol, 99% yield). $^1$H NMR (500 MHz, Acetone-d$_6$) δ 8.94 (s, 1H), 7.58 (d, J=7.3 Hz, 6H), 7.51 (d, J=7.6 Hz, 1H), 7.44 (t, J=7.3 Hz, 1H), 7.35 (t, J=7.7 Hz, 6H), 7.27 (t, J=7.3 Hz, 3H), 7.16 (s, 1H), 6.98 (d, J=7.7 Hz, 1H), 6.95 (d, J=8.6 Hz, 1H), 6.84 (d, J=2.4 Hz, 1H), 6.71 (dd, J=8.6, 2.4 Hz, 1H), 5.45 (d, J=12.7 Hz, 1H), 5.40 (d, J=12.7 Hz, 1H), 1.37 (s, 6H). $^{13}$C NMR (125 MHz, Acetone-d$_6$) δ 170.77, 159.44, 151.20, 146.77, 145.54, 144.99, 139.57, 131.10, 130.65, 129.44, 128.85, 128.58, 128.22, 127.84, 126.74, 124.13, 122.83, 122.14, 117.61, 116.74, 113.91, 103.03, 83.79, 73.53, 71.25, 53.76, 27.32.

NitroxylFluor (7).

To a solution of compound 6 (28.5 mg, 0.039 mmol, 1.0 eq) in CHCl$_3$ (10.0 mL), TFA (1.0 mL) was added at room temperature. Immediately thereafter, Et$_3$SiH (1.0 mL) was added. The solution was concentrated under reduced pressure and purified via silica gel column chromatography with 1:9 v/v EtOAc/Hexanes to afford the product as a white solid (2.50 mg, 0.0051 mmol, 13% yield). $^1$H NMR (500 MHz, Acetone-d$_6$) δ 8.94 (s, 1H), 7.52 (d, J=7.6 Hz, 1H), 7.45 (t, J=7.5 Hz, 1H), 7.33 (t, J=7.9 Hz, 1H), 7.16 (s, 1H), 6.97 (d, J=7.7 Hz, 1H), 6.94 (d, J=8.6 Hz, 1H), 6.82 (d, J=2.4 Hz, 1H), 6.70 (dd, J=8.6, 2.4 Hz, 1H), 5.46 (d, J=12.7 Hz, 2H), 5.40 (d, J=12.6 Hz, 1H), 1.80 (s, 6H), 1.22 (s, 1H). $^{13}$C NMR (125 MHz, Acetone) δ 205.30, 170.94, 158.61, 150.31, 145.88, 144.74, 143.90, 138.70, 129.79, 128.56, 127.32, 126.02, 123.24, 121.94, 121.30, 116.71, 115.90, 113.07, 102.15, 82.92, 72.70, 54.59, 44.49, 29.70. HR-MS calcd [M+H]$^+$ 489.0330, found 489.0334.

Scheme 4. Synthesis of 2-methyl-2-(tritylthio)propanoic acid (9).

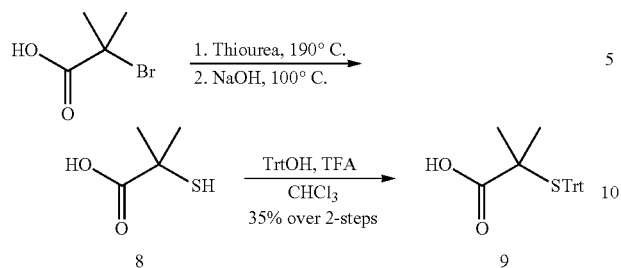

2-Mercaptoisobutryic Acid (8)

In a 100 mL round-bottom flask fitted with a reflux condenser, thiourea (4.6 g, 61 mmol, 1.0 eq) was added to neat 2-bromo isobutyric acid (10 g, 60 mmol, 1.0 eq) at 100° C. The temperature was increased to 200° C., and the reaction mixture was stirred at this temperature for 2.5 h. The reaction was cooled to room temperature, followed by the addition of 3.5 M NaOH (45 mL, 158 mmol, 2.6 eq). The reaction was placed under reflux for 2.5 h. The reaction was cooled to room temperature and washed with $Et_2O$ (3×). The aqueous layer was collected and acidified with 2M HCl, then extracted with $Et_2O$ (3×) and then dried over $Na_2SO_4$. The solution was concentrated under reduced pressure to give the title compound as a yellow oil (4.3 g) which was used directly in the following step without further purification.

2-(Mercaptotrityl)isobutryic Acid (9)

To a solution of triphenylmethanol (9.4 g, 36 mmol, 1.0 eq) and TFA (3.6 mL, 48 mmol, 1.3 eq) in $CHCl_3$ (145 mL), compound 8 (4.3 g) was added and allowed to stir at room temperature for 2 h. When the reaction was complete as judged by TLC, it was concentrated onto Celite and loaded onto a silica gel column using 1:9 v/v EtOAc/Hexanes eluent. The eluent polarity was increased to 1:1 v/v EtOAc/Hexanes then changed to 1:6 v/v $MeOH/CH_2Cl_2$ until all of the compound was eluted from the column. The resulting yellow solid was rinsed over filter paper with hexanes to yield the pure compound as a white solid (7.7 g, 21 mmol, 36% yield over two steps). $^1$H NMR (500 MHz, DMSO-$d_6$) δ 7.46 (d, J=7.8 Hz, 6H), 7.34 (t, J=7.7 Hz, 6H), 7.25 (t, J=7.3 Hz, 3H), 1.09 (s, 6H). $^{13}$C NMR (125 MHz, DMSO-$d_6$) δ 175.48, 145.18, 130.55, 128.57, 127.55, 69.05, 52.68, 40.45, 27.64.

Scheme 5. Synhtesis of NitroxyBlue-1 (11).

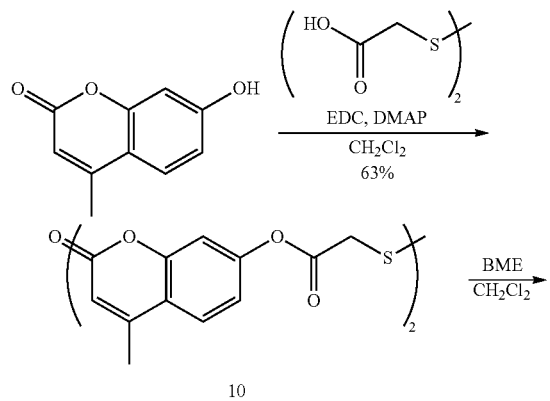

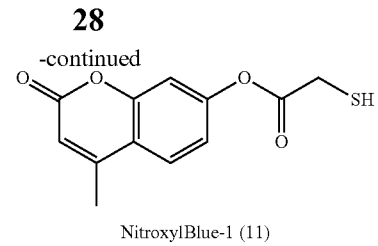

NitroxylBlue-1 (11)

Bis(4-methyl-2-oxo-2H-chromen-7-yl) 2,2'-disulfanediyldiacetate (10)

A solution of 4-methylumbelliferone (508 mg, 2.9 mmol, 2.1 eq), dithiodiglycolic acid (250 mg, 1.4 mmol, 1.0 eq), EDC hydrochloride (552 mg, 2.9 mmol, 2.1 eq), and DMAP (55 mg, 0.5 mmol, 0.3 eq) in $CH_2Cl_2$ (5 mL) was stirred at room temperature overnight. The resulting mixture was washed with brine. The organic fraction was dried over $Na_2SO_4$, concentrated and purified via silica gel column chromatography with 1:32 v/v $MeOH/CH_2Cl_2$ to yield the product as a white solid (432 mg, 0.9 mmol, 63% yield). $^1$H NMR (500 MHz, DMSO-$d_6$) δ 7.86 (d, J=8.6 Hz, 2H), 7.25 (d, J=2.2 Hz, 2H), 7.24 (s, 2H), 6.48-6.39 (m, 2H), 4.18 (s, 4H), 2.47 (s, 6H). $^{13}$C NMR (125 MHz, DMSO-$d_6$) δ 168.81, 160.41, 154.39, 153.77, 153.48, 127.47, 119.02, 118.68, 114.83, 110.76, 41.59, 40.45, 19.08.

NitroxylBlue-1 (11).

1M 2-mercaptoethanol in $CH_2Cl_2$ (50 μL, 0.05 mmol, 1.0 eq) was added to a solution of compound (10) (25 mg, 0.05 mmol, 1.0 eq) in $CH_2Cl_2$ (10 mL) and stirred at room temperature overnight. When determined to be finished by TLC, the compound was purified by silica gel column chromatography in 1:32 v/v $MeOH/CH_2Cl_2$ eluent to afford the pure product (9.6 mg, 0.4 mmol, 38% yield). $^1$H NMR (500 MHz, CDCl$_3$) δ 7.67-7.59 (m, 1H), 7.13 (d, J=2.3 Hz, 0H), 7.11 (d, J=1.4 Hz, 1H), 6.26 (d, J=1.2 Hz, 1H), 3.89 (s, 2H), 2.45-2.42 (m, 3H). $^{13}$C NMR (125 MHz, CDCl$_3$) δ 167.85, 160.66, 154.42, 153.07, 152.30, 125.93, 118.51, 118.18, 115.03, 110.67, 77.36, 42.07, 30.05, 19.10.

Scheme 6. Synhtesis of NitroxylBlue-2 (12).

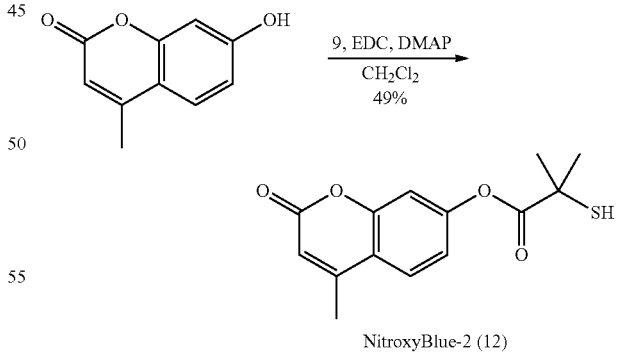

NitroxyBlue-2 (12)

NitroxylBlue-2 (12).

A solution of 4-methylumbelliferone (94.8 mg, 0.54 mmol, 1.0 eq), compound 9 (195 mg, 0.54 mmol, 1.0 eq), EDC hydrochloride (600 mg, 3.0 mmol, 6.0 eq), and DMAP (30.0 mg, 0.20 mmol, 0.4 eq) in $CH_2Cl_2$ (5 mL) was stirred at room temperature overnight. The resulting mixture was washed with brine (3×). Organics were pooled and concentrated under reduced pressure, then reconstituted in $CHCl_3$ (10 mL). To the resulting solution was added TFA (1.0 mL) at room temperature, turning the solution yellow. HSiEt₃ (1.0 mL) was added dropwise until solution turned clear. The solution was then dry loaded onto Celite and loaded onto a silica gel column then run in 1:9 v/v EtOAc/Hexanes to afford a white solid (51.1 mg, 0.18 mmol, 49% yield). $^1$H NMR (500 MHz, CDCl₃) δ 7.63 (d, J=8.6 Hz, 1H), 7.13 (d, J=2.2 Hz, 1H), 7.10 (d, J=8.6 Hz, 1H), 2.61 (s, 1H), 2.45 (s, 3H), 1.74 (s, 6H). $^{13}$C NMR (125 MHz, CDCl₃) δ 173.31, 160.75, 154.58, 153.72, 152.17, 125.77, 118.34, 118.05, 115.01, 110.56, 45.21, 29.01, 19.11.

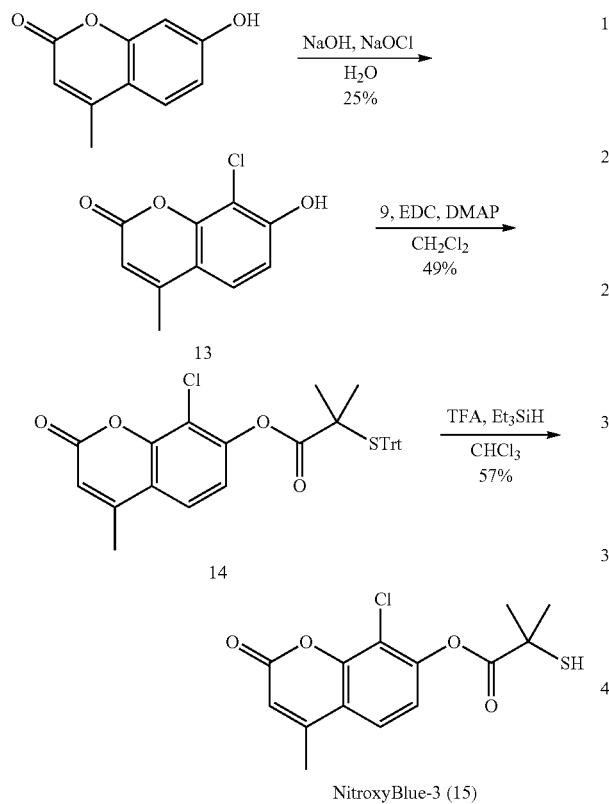

8-Chloro-7-hydroxy-4-methyl-2H-chromen-2-one (13)

5.25% wt/wt NaOCl (4 mL) was added to a solution of 4-methylumbiliferone (300 mg, 1.7 mmol, 1.0 eq) in 0.1 M NaOH (12 mL) and stirred at room temperature for 5 h. The reaction was quenched by the addition of 0.1 M HCl (30.0 mL), then extracted from Et₂O (3×), back washed brine (3×), dried over Na₂SO₄, concentrated and purified with silica gel column chromatography using 1:19 v/v MeOH/CH₂Cl₂ to yield the product as a white solid (90 mg, 0.42 mmol, 25% yield). $^1$H NMR (500 MHz, Acetone-d₆) δ 7.65 (d, J=8.8 Hz, 1H), 7.09 (d, J=8.8 Hz, 1H), 6.22 (d, J=1.2 Hz, 1H), 2.49 (s, 3H). $^{13}$C NMR (125 MHz, Acetone-d₆) δ 160.82, 158.15, 154.69, 152.71, 125.63, 125.34, 115.44, 114.01, 113.02, 19.39.

8-Chloro-4-methyl-2-oxo-2H-chromen-7-yl 2-methyl-2-(tritylthio)propanoate (14)

A solution of compound 13 (81.6 mg, 0.4 mmol, 1.0 eq), compound 9 (199.4 mg, 0.47 mmol, 1.1 eq), EDC hydrochloride (421.7 mg, 2.2 mmol, 4.4 eq), and DMAP (24.4 mg, 0.2 mmol, 0.4 eq) in CH₂Cl₂ (4 mL) was stirred at room temperature overnight. The reaction was washed with brine (3×) and the organic fraction was dried over Na₂SO₄. After concentrating under reduced pressure, the crude residue was purified by silica gel column chromatography with 1:19 v/v MeOH/CH₂Cl₂ to yield the product as a white solid (135 mg, 0.2 mmol, 49% yield). $^1$H NMR (500 MHz, Acetone-d₆) δ 7.80 (d, J=8.8 Hz, 1H), 7.67-7.60 (m, 6H), 7.37 (t, J=7.7 Hz, 6H), 7.31-7.25 (m, 3H), 6.97 (d, J=8.8 Hz, 1H), 6.45-6.41 (m, 1H), 2.56 (s, 3H), 1.48 (s, 6H). $^{13}$C NMR (125 MHz, Acetone-d₆) δ 172.17, 160.09, 154.14, 151.89, 151.33, 146.21, 131.66, 129.46, 128.54, 125.29, 120.62, 120.38, 116.13, 70.70, 53.52, 28.30, 19.47.

NitroxylBlue-3 (15).

To a solution of compound 14 (135 mg, 0.2 mmol, 1.0 eq) in CHCl₃ (10.0 mL), TFA (1.0 mL) was added at room temperature, turning the solution yellow. Et₃SiH (1.0 mL) was then added to the reaction. When the reaction was complete as judged by TLC the volatiles were removed and the crude residue was purified via silica gel column chromatography with 1:9 v/v EtOAc/Hexanes to afford a white solid (35.6 mg, 0.1 mmol, 57% yield). $^1$H NMR (500 MHz, CDCl₃) δ 7.54 (d, J=8.6 Hz, 1H), 7.16 (d, J=8.6 Hz, 1H), 6.30 (s, 1H), 2.69 (s, 7H), 2.44 (s, 3H), 1.77 (s, 6H). $^{13}$C NMR (125 MHz, CDCl₃) δ 172.49, 159.54, 152.18, 150.71, 150.02, 123.17, 119.31, 118.89, 116.01, 115.29, 77.36, 45.19, 29.15, 19.19.

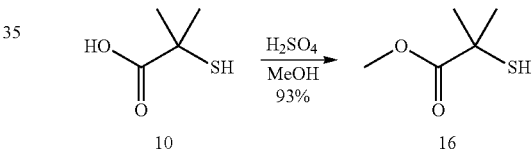

Methyl 2-mercapto-2-methylpropanoate (16)

To a solution of compound 10 (120 mg, 1.0 mmol, 1 eq) in MeOH (5 mL), was added 5 drops of concentrated H₂SO₄. The solution was allowed to stir for 5 h before it was concentrated under reduced pressure, taken up in CH₂Cl₂ (5 mL), and washed with brine (2×). The organic layer was dried over Na₂SO₄ and concentrated giving the title compound as a clear liquid with a foul odor (111 mg, 0.93 mmol, 93% yield). $^1$H NMR (500 Hz, CDCl₃) δ 3.73 (s, 3H), 2.43 (s, 1H), 1.58 (s, 6H). $^{13}$C NMR (125 MHz, CDCl₃) δ 175.90, 77.36, 53.06, 45.11, 29.38.

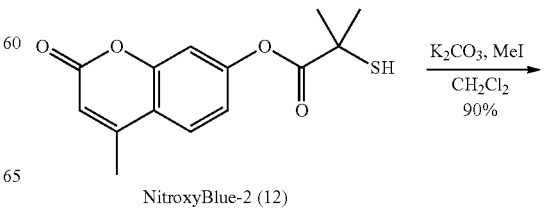

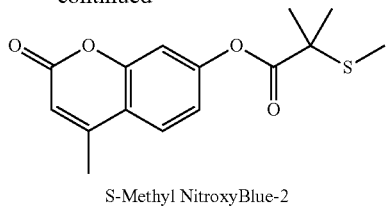

S-Methyl NitroxylBlue-2

S-Methyl NitroxylBlue-2 (17).

To a solution of NitroxylBlue-2 (100 mg, 0.359 mmol, 1 eq) in $CH_2Cl_2$ (1 mL) was added methyl iodide (22.5 µL, 0.359 mmol, 1 eq) and potassium carbonate (109 mg, 0.790 mmol, 2.2 eq.). The solution was allowed to stir for 24 h before it was diluted with $CH_2Cl_2$ (10 mL) and washed with brine (2×). The organic layer was dried over $Na_2SO_4$ and concentrated giving the title compound as a white powder (95 mg, 0.320 mmol, 90% yield). $^1$H NMR (500 Hz, $CDCl_3$) δ 7.58 (d, J=8.6 Hz, 1H), 7.06 (d, J=2.3 Hz, 1H), 7.03 (dd, J=8.7, 2.3 Hz, 1H), 6.22 (s, 1H), 2.40 (s, 3H), 2.16 (s, 3H), 1.61 (s, 6H). $^{13}$C NMR (125 MHz, $CDCl_3$) δ 171.67, 160.63, 154.36, 153.65, 152.21, 128.20, 125.70, 118.12, 118.07, 114.70, 110.49, 46.64, 24.96, 18.98, 13.2.

Example 3. Pharmaceutical Dosage Forms

The following formulations illustrate representative pharmaceutical dosage forms that may be used for the administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

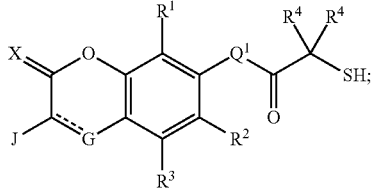

or a salt or solvate thereof, wherein
- - - - - is a single bond or a double bond;
$Q^1$ is O or S;
$R^1$, $R^2$, and $R^3$ are each independently H, halo, —($C_1$-$C_6$)alkyl, or OR wherein R is H or —($C_1$-$C_6$)alkyl;
each $R^4$ is independently H or —($C_1$-$C_6$)alkyl, or each $R^4$ taken together form —($C_3$-$C_6$)cycloalkyl;
G is —CH— or —C[($C_1$-$C_6$)alkyl]— when - - - - - is a double bond, or G is Formula IA when - - - - - is a single bond:

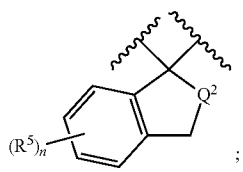

wherein
$Q^2$ is O or S;
each $R^5$ is independently H, halo, —($C_1$-$C_6$)alkyl, or $OR^a$ wherein $R^a$ is H or —($C_1$-$C_6$)alkyl; and
n is 1-4;
X is O, and J is H or —($C_1$-$C_6$)alkyl when - - - - - is a double bond; and
X and J taken together form a monocyclic aryl group when - - - - - is a single bond;
wherein the monocyclic aryl group is optionally substituted with one or more substituents.

2. The compound of claim 1 wherein the compound of Formula I is a compound of Formula II:

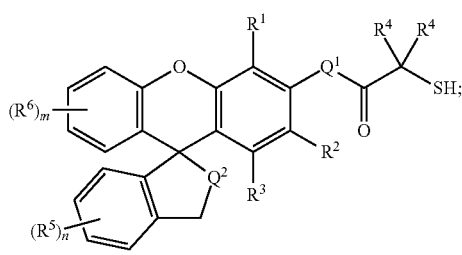

wherein
each $R^6$ is independently H, halo, —($C_1$-$C_6$)alkyl, or $OR^b$ wherein $R^b$ is H or —($C_1$-$C_6$)alkyl; and
m is 1-4.

3. The compound of claim 2 wherein the compound of Formula II is a compound of Formula IIB:

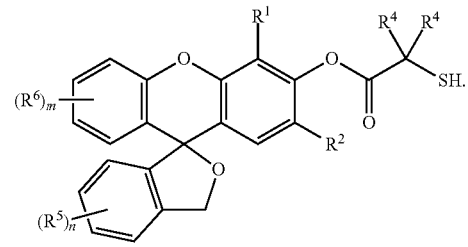

4. The compound of claim 2 wherein the compound of Formula II is a compound of Formula IIC:

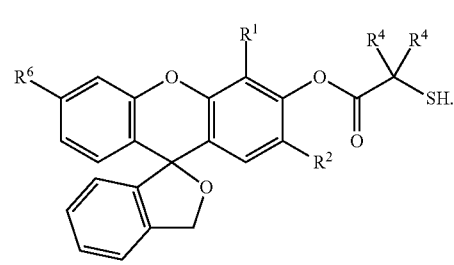

5. The compound of claim 4 wherein:
$R^1$ and $R^2$ are each independently H, halo, OH, or —O($C_1$-$C_6$)alkyl;
$R^4$ is —($C_1$-$C_6$)alkyl, or each $R^4$ taken together form —($C_3$-$C_6$)cycloalkyl; and
$R^6$ is halo, OH, or —O($C_1$-$C_6$)alkyl.

6. The compound of claim 4 wherein:
$R^1$ and $R^2$ are halo;
$R^4$ is —($C_1$-$C_6$)alkyl, or each $R^4$ taken together form —($C_3$-$C_6$)cycloalkyl; and
$R^6$ is halo or OH.

7. The compound of claim 4 wherein the compound is:

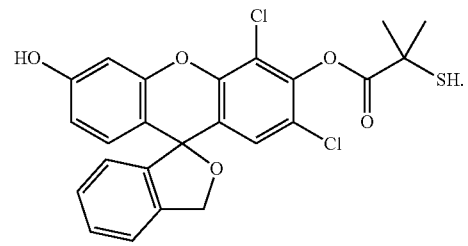 [SMILES: CC(C)(S)C(=O)Oc1c(Cl)cc2c(c1Cl)Oc1cc(O)ccc1C21OCc2ccccc21]

8. The compound of claim 1 wherein the compound of Formula I is a compound of Formula III:

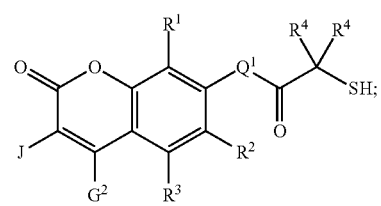

wherein
R¹, R², and R³ are each independently H, halo, or —(C₁-C₆)alkyl;
G² is H or —(C₁-C₆)alkyl; and
J is H or —(C₁-C₆)alkyl.

9. The compound of claim 8 wherein Q¹ is O.

10. The compound of claim 8 wherein R¹ and R² are each independently H or halo.

11. The compound of claim 8 wherein R³ is H and G² is —(C₁-C₆)alkyl.

12. The compound of claim 8 wherein J is H.

13. The compound of claim 8 wherein:
Q¹ is O;
R¹ and R² are each independently H or halo;
R³ and J are H; and
R⁴ and G² are —CH₃.

14. A method for imaging nitroxyl comprising:
a) contacting a sample with a compound according to claim 1 to form a mixture; and
b) detecting the presence or absence of a change in fluorescent intensity in the mixture;
wherein the thiol moiety of the compound covalently bonds to nitroxyl when present in the sample to form a —S(NH)OH intermediate, and the intermediate intramolecularly cyclizes at the carbonyl moiety (—C(=O)—) and cleaves the Q¹-carbonyl bond to release a xanthene moiety or a coumarin moiety as a fluorescent molecule;
thereby imaging nitroxyl in the sample when the fluorescent molecule changes the fluorescent intensity of the mixture.

15. The method of claim 14 wherein the fluorescent molecule is Formula Y or Formula Z:

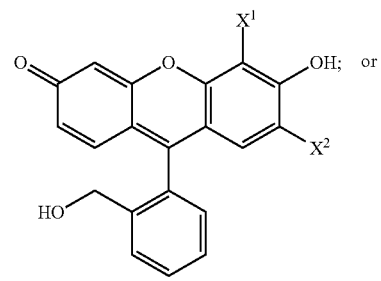

(Y)

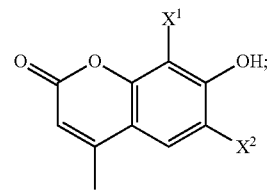

(Z)

wherein X¹ and X² are independently H or halo.

16. The method of claim 14 wherein the fluorescent molecule has greater fluorescence than the compound.

17. The method of claim 14 wherein the fluorescent molecule has an absorbance and emission profile that is in the visible spectrum.

18. The method of claim 14 wherein the compound is more reactive toward nitroxyl than biological thiols.

* * * * *